(12) United States Patent
Chis

(10) Patent No.: US 10,238,115 B2
(45) Date of Patent: Mar. 26, 2019

(54) ANTIMICROBIAL MATERIAL AND USES THEREOF

(71) Applicant: Claire Technologies, LLC, Morrisville, NC (US)

(72) Inventor: Cristian Vasile Chis, Creedmoor, NC (US)

(73) Assignee: Claire Technologies, LLC, Morrisville, NC (US)

( * ) Notice: Subject to any disclaimer, the term of this patent is extended or adjusted under 35 U.S.C. 154(b) by 0 days.

(21) Appl. No.: 14/150,284

(22) Filed: Jan. 8, 2014

(65) Prior Publication Data

US 2014/0120148 A1 May 1, 2014

Related U.S. Application Data

(63) Continuation of application No. PCT/EP2011/061689, filed on Jul. 8, 2011.

(51) Int. Cl.
*A01N 59/16* (2006.01)
*C02F 1/28* (2006.01)
*C02F 1/50* (2006.01)

(52) U.S. Cl.
CPC .............. *A01N 59/16* (2013.01); *C02F 1/288* (2013.01); *C02F 1/281* (2013.01); *C02F 1/505* (2013.01)

(58) Field of Classification Search
None
See application file for complete search history.

(56) References Cited

U.S. PATENT DOCUMENTS

| | | | | |
|---|---|---|---|---|
| 5,961,843 A | * | 10/1999 | Hayakawa | A01N 25/26 210/192 |
| 6,180,548 B1 | * | 1/2001 | Taoda et al. | 501/137 |
| 2003/0113255 A1 | | 6/2003 | Harlan | |
| 2008/0118539 A1 | * | 5/2008 | McDow et al. | 424/404 |

FOREIGN PATENT DOCUMENTS

| | | |
|---|---|---|
| CN | 1159741 A | 9/1997 |
| CN | 103997890 B | 12/2016 |
| EP | 0804877 A1 | 5/1997 |
| EP | 2729001 B1 | 12/2017 |
| JP | 08133919 | 5/1996 |
| JP | 2006069935 | 3/2006 |

OTHER PUBLICATIONS

Hayakawa et al. Translation of JP 08133919, accessed Jan. 2, 2015.*
Brunauer et al., Adsorption of Gases in Multimolecular Layers, The Journal of the American Society, 1938, vol. 60, pp. 309-319.
Lok et al., Silver nanoparticles: partial oxidation and antibacterial activities, 2007, Journal of Biological Inorganic Chemistry, vol. 12, 527-534.
Rai et al., Silver nanoparticles as a new generation of antimicrobials, 2009, Biotechnology Advances, vol. 27: 76-83.
Silvestry-Rodriguez et al., Silver as a Residual Disinfectant to Prevent Biofilm Formation in Water Distribution Systems, 2008, Applied and Environmental Microbiology, vol. 74 (No. 5):1639-1641.
International Search Report for PCT/EP2011/061689, International filing date Aug. 7, 2011, dated Dec. 10, 2011.
Database WPI, Week 200621, Thomson Scientific, London, GB, p. 1-2.
Database WPI, Week 199631, Thomson Scientific, London, GB, p. 1-2.
The Merck Index, An Encyclopedia of Chemicals, Drugs, and Biologicals, 14th edition, 2006, Whitehouse Station, NJ, Silver(II) Oxide, p. 1469.
IPRP and Written Opinion for International Application No. PCT/EP2011/061689 dated Jan. 14, 2014.
European Decision to Grant for European Application No. 11730323.0 dated Nov. 23, 2017.
Chinese Office Action for Chinese Application No. 201180072193 dated Jan. 21, 2015; retrieved from Global Dossier on Oct. 26, 2018.
Chinese Office Action for Chinese Application No. 201180072193 dated Sep. 22, 2015; retrieved from Global Dossier on Oct. 26, 2018.
Chinese Office Action for Chinese Application No. 201180072193 dated Mar. 21, 2016; retrieved from Global Dossier on Oct. 26, 2018.
Chinese Decision to Grant for Chinese Application No. 201180072193 dated Sep. 1, 2016; retrieved from Global Dossier on Oct. 26, 2018.
European Office Action for European Application No. 11730323.0 dated Feb. 27, 2015; retrieved from Global Dossier on Oct. 26, 2018.
European Office Action for European Application No. 11730323.0 dated Nov. 30, 2015; retrieved from Global Dossier on Oct. 26, 2018.
European Office Action for European Application No. 11730323.0 dated Oct. 27, 2016; retrieved from Global Dossier on Oct. 26, 2018.

* cited by examiner

*Primary Examiner* — Nicole P Babson
(74) *Attorney, Agent, or Firm* — Jenkins, Wilson, Taylor & Hunt, P.A.

(57) ABSTRACT

An antimicrobial material, antimicrobial devices and method of reducing or eliminating microorganisms from a fluid susceptible to contain microorganisms is presented. The antimicrobial material is comprised of a porous activated ceramic substrate; a titanium dioxide layer covalently bound to the ceramic substrate; and a silver salt layer covalently bound to the titanium oxide layer. This antimicrobial material is used in the antimicrobial devices and methods to reduce or eliminate microorganisms in fluid.

13 Claims, 10 Drawing Sheets

ANTIMICROBIAL MATERIAL AND USES THEREOF

CROSS REFERENCE TO RELATED APPLICATIONS

This application is a continuation of and claims priority to International Application No. PCT/EP2011/061689, entitled "Antimicrobial Material and Uses Thereof", filed Jul. 8, 2011, the contents of which are hereby incorporated by reference.

FIELD OF THE INVENTION

The present invention relates to the field of fluid decontamination, particularly water, microbial decontamination.

BACKGROUND OF THE INVENTION

Exposing the public to water contaminated with microorganisms, which includes drinking water and non-drinking water, represents a serious health problem. There is a general need for improved materials and methods to eliminate microorganisms from fluids for various applications, including the provision of safe or potable drinking water as well as the provision of microorganism-free water to various devices or systems, which include drinking water treatment plants, air conditioning systems and swimming pools.

Biocidal agents commonly used in water disinfection encompass halogens, ozone, U.V., quaternary amine compounds, hydrogen peroxide, sodium monopersulphate, and metal ions.

The use of metals for water disinfection is known from antiquity, and has recently increased, due notably to the fact that microorganisms have acquired resistance to usual treatments. The biostatic/biocidal properties of metal ions such as silver, copper and zinc are well known in the art. Antimicrobial effects of metal ions have been shown in the art for a variety of bacteria (including $E.\ coli,\ S.\ aureus,\ S.\ epidermis,\ S.\ pneumoniae,\ P.\ aeruginosa$), viruses (including Herpes simplex, HIV, Nile virus), fungi ($A.\ niger,\ C.\ albicans$) and micro-algae. So far, metal ions have been used for this purpose under various forms, such as metal colloids (salts, oxides) or alloys. In some prior art embodiments, water treatment using metal ions was performed using metal salts, in which case the rapid consumption of the ions reduced the longevity of the disinfectant effect. Notably, metal ions are readily complexed with organic matter in the contaminated water and they become unavailable for killing microorganisms. According to the prior art methods, a continuous production of metal ions was needed to generate an effective and long term antimicrobial effect.

Owing to their strong oxidant properties, cationic forms of various heavy metals such as $As^+$, $Pb^{2+}$, $Cd^{2+}$, $Hg^{2+}$ and $Cr^{6+}$ have been discussed for their toxicity towards microorganisms. The antimicrobial activity of these cationic entities has been ascribed to their electron attraction effect upon contact with the microorganism membranes inducing membrane alterations that cause the death of the microorganisms.

Sterilizing power of other metals such as copper, gold and platinum was also known in the art. Also, colloidal silver is widely recognized in the art as a relevant antimicrobial agent. It has been shown in the art that silver is active at least against 650 distinct microorganisms species, which allows to classify silver as a broad spectrum antimicrobial agent. It is noticed that silver particles have been used in the art as antibiotic active ingredient. Silver has been shown to be effective against numerous pathogenic bacteria, including antibiotics-resistant pathogenic bacteria, as well as numerous protozoa and viruses.

Silver has also been reported to delay or prevent the formation of biofilms in medical catheters, prosthetic heart valves, vascular grafts and fracture fixation devices. Silver has also been used in water filters, cooling towers and water distribution systems. In all these applications, silver exerts its antimicrobial effect by progressive elution from the devices.

Noticeably, silver released under the form of its silver nitrate salt has been found ineffective to prevent biofilm formation in water distribution systems (Silvestry-Rodriguez et al., 2008, Applied and Environmental Microbiology, Vol. 74 (no 5): 1639-1641).

Actual mechanisms that underlie the microbicidal effect of silver have not yet been unequivocally deciphered. Some authors have shown that the bactericidal activity of silver is mediated by its binding to disulfide or sulfhydryl groups in cell wall proteins. Other authors have shown that silver also binds to DNA. According to some scientific works, silver must be under its ionized form, i.e. in its cationic form, to exert antimicrobial properties (Lok et al., 2007, Journal of Biological inorganic Chemistry, Vol. 12 (no 4): 527-534; Rai et al., 2009, Biotechnology Advances, Vol. 27: 76-83).

There is still a need in the art for alternative or improved antimicrobial materials and systems for the purpose of treatment of various fluids, particularly aqueous media, including water.

SUMMARY OF THE INVENTION

The present invention relates to a multi-layered antimicrobial material and to uses thereof, notably for reducing or removing microorganism.

This invention concerns an antimicrobial material that is comprised of a porous activated ceramic substrate, a titanium dioxide layer that is covalently bound to the ceramic substrate, and a silver salt layer that is covalently bound to the titanium oxide layer.

In some embodiments, the porous activated ceramic substrate comprises, or consists of, activated alumina.

In some embodiments, the porous activated ceramic substrate has a surface area of more than 150 $m^2 \cdot g-1$, and preferably of more than 250 $m^2 \cdot g-1$.

In some embodiments, the thickness of the titanium dioxide layer is lower than 20 nanometers, preferably lower than 10 nanometers, and is most preferably equal to, or lower than, 5 nanometers.

In some embodiments, the silver salt consists of a silver halide, which encompasses silver chloride.

In some embodiments, the silver salt layer is of less than 10% by weight, based on the total weight of the antimicrobial composition.

This invention also pertains to a method for preparing an antimicrobial material comprising the steps of: a) providing a porous activated ceramic substrate; b) reacting the surface area of the porous activated ceramic substrate with titanium dioxide, so as to obtain a titanium dioxide-coated solid ceramic substrate; and depositing a silver salt layer on the titanium dioxide-coated porous activated ceramic substrate obtained at step b), so as to obtain the antimicrobial solid material.

The instant invention also concerns a method for reducing or eliminating microorganisms from a fluid susceptible to contain microorganisms, comprising a step of bringing into contact the fluid with an antimicrobial material as defined above.

The present invention also deals with an antimicrobial device comprising: a) means for circulating a fluid to be decontaminated, the means comprising (i) fluid inlet means, (ii) a decontamination vessel and (iii) fluid outlet means, wherein the inlet means are in fluid communication with the decontamination vessel and wherein the antimicrobial chamber is in fluid communication with the fluid outlet means; b) an effective amount of an antimicrobial material as defined above which is confined in the decontamination vessel.

DETAILED DESCRIPTION OF THE INVENTION

Figure 1:
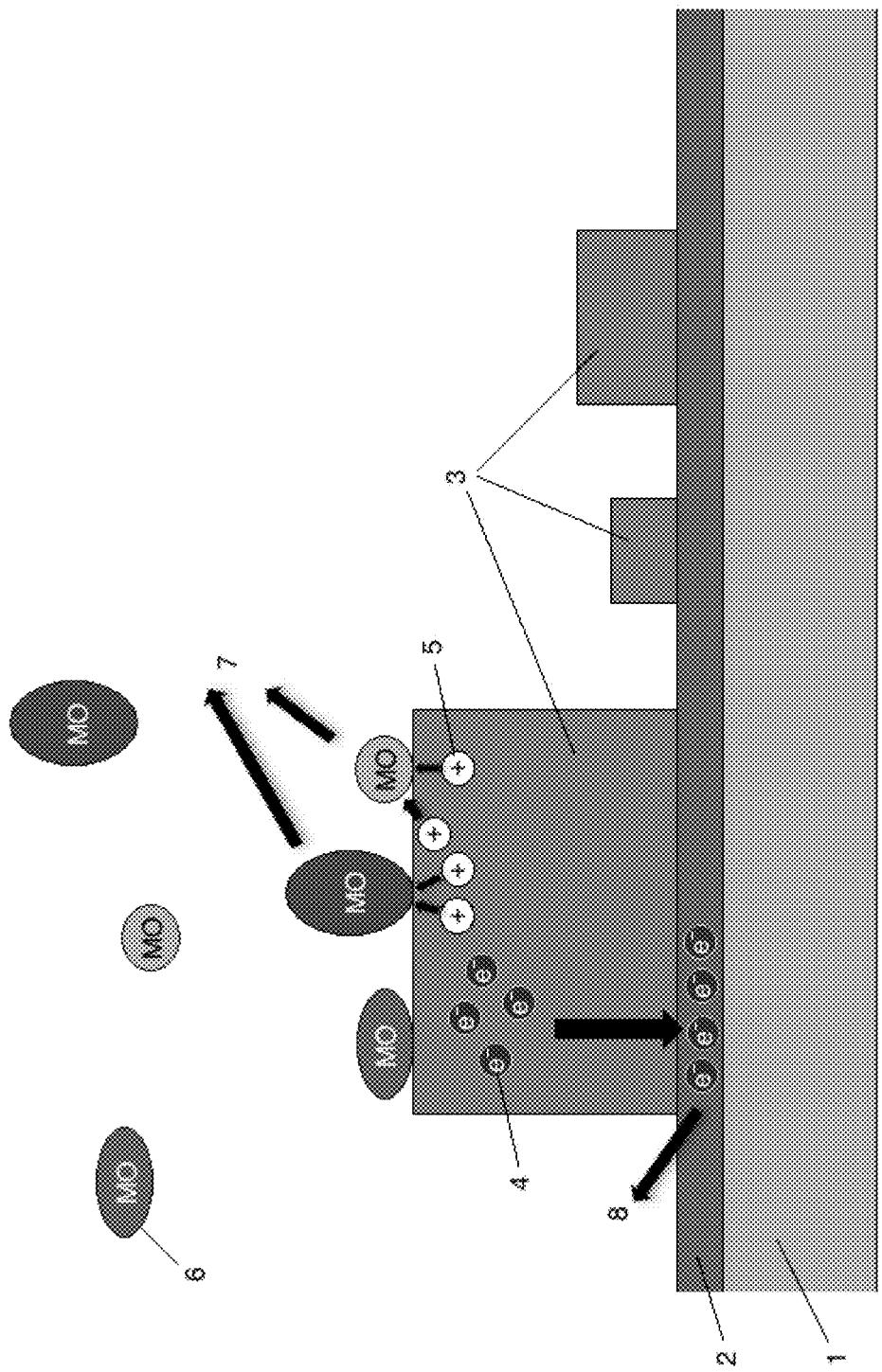
FIG. 1 is a schematic drawing of an antimicrobial material disclosed in the specification. (1): external portion of the porous activated ceramic substrate. (2): titanium dioxide continuous layer that is covalently bound to the porous activated ceramic substrate. (3) silver salt discontinuous layer of silver salt nano-aggregates that is covalently bound to the titanium dioxide layer. One covalently bound silver salt aggregate is artificially magnified in FIG. 1 for the purpose of detailing some features of the antimicrobial material. (e−): schematic representation of an electron. (+): schematic representation of a positive charge. (MO; 6) schematic representation of a microbe (also termed microorganism). As disclosed in FIG. 1, the killing of the microorganisms (MO) is caused rapidly after their contact with the discontinuous silver salt layer by electronic discharge performed by the cationic state (+; 5) of the discontinuous silver salt layer. Once killed by contact, the dead microorganism cells detached form the surface of the antimicrobial material (7). The electrons originating from the microorganisms (e−; 4) are captured by the discontinuous silver salt layer and then transiently stored within the titanium dioxide continuous layer, before being released in the external environment (8).
Figure 2:
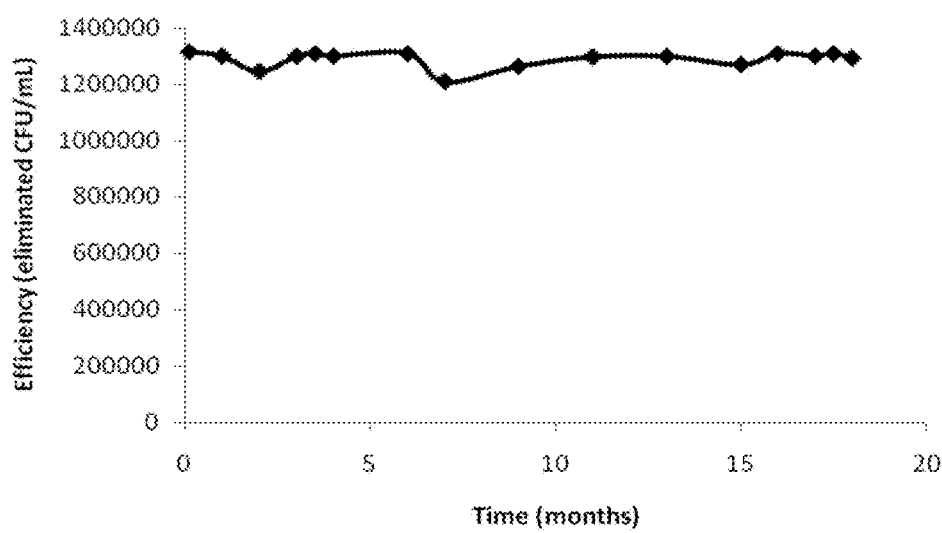
FIG. 2 illustrates the efficiency of an antimicrobial material disclosed herein. Abscissa: time period of use expressed as the number of months. Ordinate: antimicrobial efficiency expressed as number of bacteria CFU (Colony Forming units) per mL.
Figure 3:
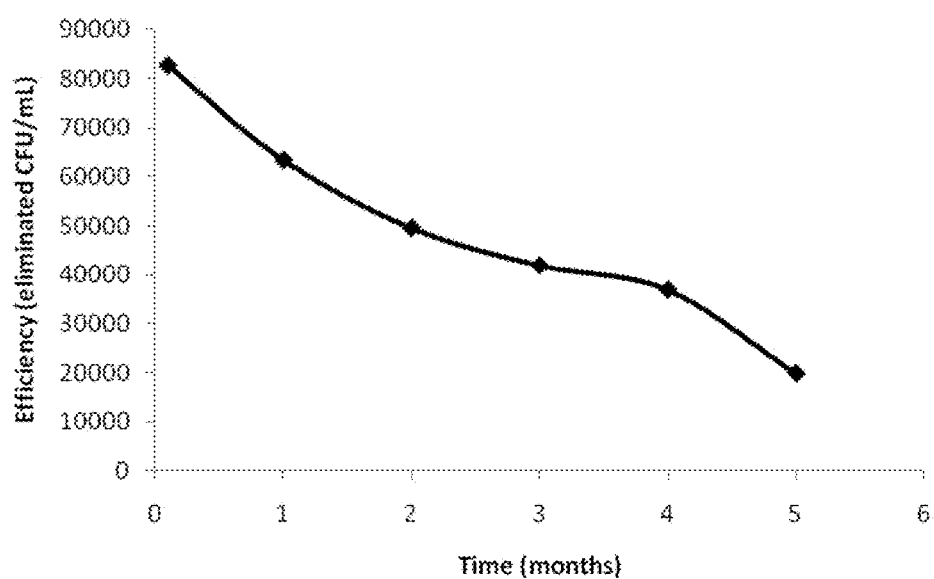
FIG. 3 illustrates the efficiency of a comparative material comprising a silver salt/titanium dioxide bilayer covalently bound to a polyethylene substrate. Abscissa: time period of use expressed as the number of months. Ordinate: antimicrobial efficiency expressed as number of bacteria CFU (Colony Forming units) per mL.

One aim of the present invention was to provide a chemically stable antimicrobial material which shall be sufficiently effective to reduce or completely kill microorganisms from fluids, particularly an aqueous fluid, and that is useful for the treatment of high volumes of those fluids.

Another aim of the present invention was to design an antimicrobial material, which remains active against microorganisms during a long period of time, e.g. at least during several months, without requiring any step of regeneration.

Still another aim of the present invention was to make publicly available an antimicrobial material that does not release harmful substances upon its contact with the fluid to be treated.

Yet another aim of the present invention was to obtain an antimicrobial material that causes microorganism death very rapidly, without requiring a long time period of contact of the microorganisms cells therewith to be effective.

Highly surprisingly, it is shown herein that these aims have been reached through the conception of a multi-layer material exposing permanently silver ions at its surface.

The present invention provides an antimicrobial material comprising: a porous activated ceramic substrate, a titanium dioxide layer that is covalently bound to the ceramic substrate, and a silver salt layer that is covalently bound to the titanium oxide layer.

As it is shown in the examples herein, the antimicrobial material described above possesses a microbicidal efficiency always exceeding the killing of 95% the microorganisms present, and in most cases exceeding the killing of 99% of the microorganisms present.

Further, it is shown herein that the antimicrobial material has a very large spectrum of biocidal activity, since it is highly active against various kinds of unrelated microorganisms, such as bacteria, fungi, algae, and amoeba. It has been found notably that the antimicrobial material according to the invention possesses a high antimicrobial efficiency against Gram+ bacteria such as *S. aureus*, Gram− bacteria such as *L. adelaidensis* (i.e. a surrogate of *L. pneumophilia*), yeasts such as *C. albicans* and algae such as *Anabena constricta*. It is noticed that the antimicrobial material is active against bacteria and fungi that are pathogenic for mammals, especially human.

Still further, it is shown herein that the biocidal efficiency of the antimicrobial material described above is exerted in real life operating conditions, including for decontaminating swimming pool water and for decontaminating the condensation water produced when functioning air conditioning systems.

It has been also shown that the antimicrobial efficiency of the antimicrobial material of the invention largely exceeds the biocidal activity, which is required for a biocidal agent to comply with the regulatory standards, which proves the actual industrial usefulness of the material.

It has also been shown that the antimicrobial material according to the invention may be used for long time periods, i.e. 20 months or more, with an unchanged antimicrobial efficiency.

It has also been shown that the antimicrobial material according to the invention causes the killing of the microorganisms after only several seconds of contact of the microorganism cells with its external surface exposing the silver salt layer.

As it will be disclosed in detail further in the present specification, the specific combination of features of the antimicrobial material described above allows the permanent presence of cationic silver at the external surface of the material, which cationic silver consists of the predominant, if not the sole, antimicrobial effective agent of the antimicrobial material.

As it will be also further detailed herein, some embodiments of the antimicrobial material include a nanometric titanium dioxide layer as well as a nanometric silver salt layer. According to the applicant's knowledge, the manufacture of a chemically stable cationic silver-based complex nanocomposite material is disclosed for the first time herein.

Notably, the inventors have found that a way for stably immobilizing a silver layer, and more precisely a cationic silver layer, on a relevant substrate was to interpose an intermediary layer, preferably a nanometric intermediary layer, between (i) the relevant substrate and (ii) the silver layer. According to the invention, the stable immobilization of the silver salt layer is obtained by covalently bonding the intermediary layer onto the relevant substrate, so as to provide a stable recipient material onto which the silver salt layer is then also stably immobilized by covalent bonding.

As it will be understood from the detailed description of the invention below, the biocidal efficiency of the antimicrobial material is also provided by the compatibility of the combined (i) substrate material, (ii) intermediary layer and (iii) silver salt layer, since none of the above means (i), (ii) and (iii) can be replaced by another kind of material without drastically affecting the biocidal properties of the corresponding final product, as it is shown in the examples herein.

As used herein, the terms "antimicrobial", "microbicidal" and "biocidal" may be used interchangeably.

As used herein, an "antimicrobial" material consists of a material exerting an "antimicrobial activity". As used herein, the term "antimicrobial activity" refers to the property or capability of a material to inactivate microorganisms. Non-limiting examples of microorganisms include Gram+ and Gram− bacteria, spore and non-spore forming bacteria, vegetative and non-vegetative fungi, yeast, protozoa, micro-algae and viruses. This "inactivation" renders the microorganism incapable of reproducing and therefore incapable of infecting other organisms and occurs by disruption of the bacteria, fungi, micro-algae or protozoa membrane, or by denaturation of the protein such as that which forms the protective capsid for viruses.

As used herein, the term "broad spectrum antimicrobial activity" refers to the property or capability of a material to inactivate numerous different, or substantially all, types of microorganisms including bacteria (and its corresponding spores), fungi, protozoa, micro-algae and viruses. An antimicrobial agent that inactivates only a selected group of microorganisms (e.g., either only gram positive cells or only gram negative cells) does not have broad spectrum antimicrobial activity.

As used herein, "activated ceramic" encompasses an aluminium oxide-based material, wherein the surface thereof possesses reactive functional groups having the ability to react with titanium dioxide precursors, which reactive functional groups mainly comprise hydroxyl groups (OH). Activated ceramic encompasses activated alumina ($Al_2O_3$).

A porous ceramic surface is understood herein to consist of a ceramic composition having a predetermined porosity to enable an optimal specific surface area allowing layering with desired functional substances.

Activated alumina is characterized notably by the number of available active sites. The surfaces contain hydroxyl groups, oxides and aluminum ions. The three basic catalytic sites also have many possible logistical combinations. Activated alumina may be prepared according to various methods known by the one skilled in the art. Generally, activated alumina may be manufactured from aluminium hydroxide by dehydroxylating the aluminium hydroxide in operating conditions allowing the production of highly porous material that is endowed with high surface area. Illustratively, activated alumina may be prepared following the method disclosed in US 2003/113255.

As used herein, a "silver salt" encompasses silver halide, silver nitrate, silver sulphate, silver carbonate, silver silicate, silver oxide and silver hydroxide. As used herein, a "silver halide" is selected from the group consisting of silver chloride, silver fluorine, silver bromine and silver iodide.

The antimicrobial material according to the invention consists of a solid material that can be manufactured in various shapes. As it is readily understood, the shape of the antimicrobial material is provided by the shape of the core of the porous activated ceramic on which the titanium dioxide intermediate layer and the silver salt external layer are deposited. In some embodiments, the antimicrobial material is under the form of granules, pellets, beads, cylinders, plates or any other shape.

In preferred embodiments, the whole surface of the activated ceramic substrate is covered with the titanium dioxide/silver salt bi-layer.

In some embodiments, only a portion of the surface of the activated ceramic substrate is covered with the titanium dioxide/silver salt bi-layer. Illustratively, in embodiments wherein the antimicrobial material is under the form of a blade having two main surfaces, (i) the two main surfaces of the activated ceramic may be coated with the titanium dioxide/silver salt bi-layer or (ii) only one main surface, or even only a portion thereof, may be coated with the titanium dioxide/silver salt bi-layer. According to the invention, porous activated ceramic material has been selected by the inventors because activated ceramic possesses a high thermal and chemical stability, and also possesses a high specific surface area. Owing to the presence of an optimal density of reactive chemical groups at its surface, mainly hydroxy groups, and owing to its optimal specific surface area, the porous activated ceramic has proved herein to be adapted for its further covalent continuous coating with the titanium dioxide layer.

In preferred embodiments, the porous activated ceramic substrate has a specific surface area of more than 150 $m^2 \cdot g-1$ and of less than 700 $m^2 \cdot g-1$. Such a specific surface area of the porous activated ceramic substrate allows to obtain a final antimicrobial material having itself a high specific surface area, i.e. a high amount of silver salt per unit of surface area that exerts an antimicrobial activity. In some preferred embodiments, the porous activated ceramic has a specific surface area of more than 250 $m^2 \cdot g-1$.

Preferably, the specific surface area value of a material may be determined using the BET method, which is well known from the one skilled in the art. Preferably, the specific surface area value of a material is determined using the specifications disclosed in ASTM D 3663-78, which is based on the method disclosed by Brunauer et al. (1938, The Journal of the American Society, 60, 309).

As used herein, porous activated ceramic substrates having a specific surface area of more than 150 $m^2 \cdot g-1$ encompasses those having a specific surface area of more than 150, 160, 170, 180, 190, 200, 210, 220, 230, 240, 250, 260, 270, 280, 290, 300, 310, 320, 330, 340 or 350 $m^2 \cdot g-1$.

As used herein, porous activated ceramic substrates having a specific surface area of less than 700 $m^2 \cdot g-1$ encompasses those having a specific surface area of less than 650, 600, 550, 500 or 450 $m^2 \cdot g-1$.

In preferred embodiments, the specific surface area ranges from 150 $m^2 \cdot g-1$ to 350 $m^2 \cdot g-1$.

According to the invention, the use of a porous activated ceramic having a specific surface area of less than 150 $m^2 \cdot g-1$ does not allow the production of a final antimicrobial material having the required antimicrobial activity.

It shall be understood that, at least theoretically, the higher the specific surface area, the higher the amount of silver salt in a given surface of an antimicrobial material according to the invention, and thus also the higher the antimicrobial activity of the antimicrobial material.

However, the inventors have found that a continuous titanium dioxide layer could not be formed on a porous activated ceramic substrate having a specific surface area of 700 $m^2 \cdot g-1$ or more. The inventors have found that, with porous activated ceramic substrates having 700 $m^2 \cdot g-1$ or more, only titanium dioxide aggregates, i.e. titanium dioxide magroaggregates, are formed at the substrate surface, instead of a continuous layer.

According to other aspects of the present invention, an optimal antimicrobial material may comprise a porous activated ceramic substrate possesses optimal pore size values.

In some embodiments, the porous activated ceramic substrate has a mean pore size ranging from 0.008 µm to 0.1 µm, which encompasses a mean pore size ranging from 0.01 to 0.05 µm, as well as a mean pore size ranging from 0.01 µm to 0.02 µm.

Preferably, the pore size distribution is narrow, which means that the porous activated ceramic substrate possesses an homogenous pore size distribution.

Illustratively, an optimal porous activated ceramic substrate encompasses such a substrate where more than 97% of the total pore volume has a pore size ranging from 0.008 µm to 0.014 µm and a mean pore size of 0.012 µm. Such an optimal porous activated ceramic substrate, as it is illustrated in the examples herein.

It shall be understood that there is no compulsory relationship between the specific surface area value and the pore size value in a porous material.

Illustratively, the present inventors have found that a candidate substrate material, like a silica substrate having a specific surface area of about 290 $m^2 \cdot g-1$, was ineffective as a substrate material for preparing an antimicrobial material possessing a continuous titanium dioxide layer, because of its too much small mean pore size, i.e. of 0.006 µm.

Pore size characteristics of a porous activated ceramic substrate used according to the invention may be easily determined by the one skilled in the art, notably by performing the BET method that has been referred to previously in the instant specification in connection with the determination of specific surface area values.

In preferred embodiments, the porous activated ceramic substrate (i) possesses a specific surface area ranging from 150 $m^2 \cdot g-1$ to 350 $m^2 \cdot g-1$ and (ii) possesses a mean pore size 0.008 µm to 0.1 µm. In most preferred embodiments, the mean pore size is of about 0.012 µm. In most preferred embodiments of the porous activated ceramic substrate, more than 90% of the pores possess the mean pore size, which includes more than 92%, 93%, 94%, 95%, 96% or 97% of the pores that possess the mean pore size value.

As shown in the examples herein, substrate materials other than porous activated ceramic are useless for manufacturing antimicrobial materials having the required activity, especially long term antimicrobial activity. Illustratively, a comparative material comprising (i) a polymeric substrate (ii) a titanium dioxide layer covalently bound thereto and (iii) a silver salt layer covalently bound to the titanium dioxide layer has a significant lower antimicrobial activity than the antimicrobial material according to the invention, yet at the first day of use for treating contaminated water. The examples herein also show that the antimicrobial activity of the polymeric substrate-based comparative material significantly decreases yet during the first week of use, to reach a decrease in antimicrobial activity of more than 50% of the initial activity after a three-month time period of use.

In contrast, the examples show that the antimicrobial activity of the antimicrobial material according to the invention remains unchanged, even after an uninterrupted use for a period of time of more than 20 months.

In preferred embodiments, the thickness of the titanium dioxide layer is lower than 50 nanometers, preferably lower than 10 nanometers, and is most preferably equal to, or lower than, 5 nanometers. It is specified that the coating of the selected substrate with a titanium dioxide layer which is at the same time (i) continuous over the whole surface portion of the substrate coated therewith, (ii) nanometric and homogenous in thickness and (iii) dense is rendered technically feasible by the specific chemical and physical characteristics of the selected substrate, i.e. mainly because the selected substrate is activated and possesses reactive hydroxy groups at its surface and also because the selected substrate is porous and thus possesses suitable specific surface area characteristics, and optionally also optimal pore size characteristics.

Generally, the thickness and the shape of the titanium dioxide layer may vary depending of the specific surface area value, the porous volume and the pore size of the activated ceramic material which is used.

According to an important feature of the antimicrobial material of the invention, the titanium dioxide layer forms a continuous coating covering the whole surface portion of the porous activated ceramic substrate with which it has been reacted. This important feature means that the titanium dioxide-coated surface portion of the substrate is at no place exposed to the external environment. Considering the final antimicrobial product, this feature involves that the titanium dioxide-coated surface portion of the substrate is at no place exposed (i) to the silver salt coating nor (ii) to the external environment. For exerting effective biocidal properties, the antimicrobial material according to the invention shall expose a required amount of cationic silver at its surface. Further, the cationic silver shall also be homogeneously distributed on the whole titanium dioxide layer, so as to provide the required level of biocidal properties at every titanium dioxide-coated surface location. These biocidal properties requirements are met herein, since the presence of a continuous titanium coating allows the covalent binding of a homogeneously distributed relevant amount of silver salt.

The one skilled in the art may easily adapt the thickness of the titanium dioxide layer so as to obtain a continuous layer, irrespective of the specific surface area value, and also irrespective of the pore size, of the porous activated ceramic substrate. Illustratively, for manufacturing an antimicrobial material according to the invention, when using a porous activated ceramic substrate having a low specific surface area of 150 m$^2$·g−1, the one skilled in the art may apply a titanium dioxide layer with a very low thickness, e.g. of about 3 nanometers. Also illustratively, when using a porous activated ceramic substrate of a higher specific surface area of 250 m$^2$·g−1, the one skilled in the art may apply a titanium dioxide coating of a higher thickness value, e.g. of 5 nanometers, so as to obtain a continuous titanium dioxide layer all over the desired portion of the substrate, wherein the titanium dioxide layer is uninterruptued including at the surface of the pores of the substrate material.

As shown in the examples herein, applying on the substrate a titanium dioxide layer of more than 50 nanometers, e.g. a titanium dioxide layer of 100-500 nanometers or more, does not allow the manufacturing of an effective antimicrobial material. As shown herein, a comparative material comprising (i) a porous activated ceramic substrate, (ii) a high thickness (more than 50 nanometers) titanium dioxide layer that is covalently bound thereto and (iii) a silver salt layer that is covalently bound to the titanium dioxide layer, is not endowed with an effective antimicrobial activity. Such a comparative material rapidly losses its residual antimicrobial activity, and the examples show that almost no antimicrobial activity remains after a one hour time period of use. Such a comparative material possesses a low initial antimicrobial activity, which may be of 30% the antimicrobial activity that is measured in the same conditions for the antimicrobial material according to the invention. Further, the examples herein also show that such a comparative material rapidly loses its residual antimicrobial activity, with e.g. a 50% loss of the initial residual activity after a one-month time period of use.

Figure 4B:
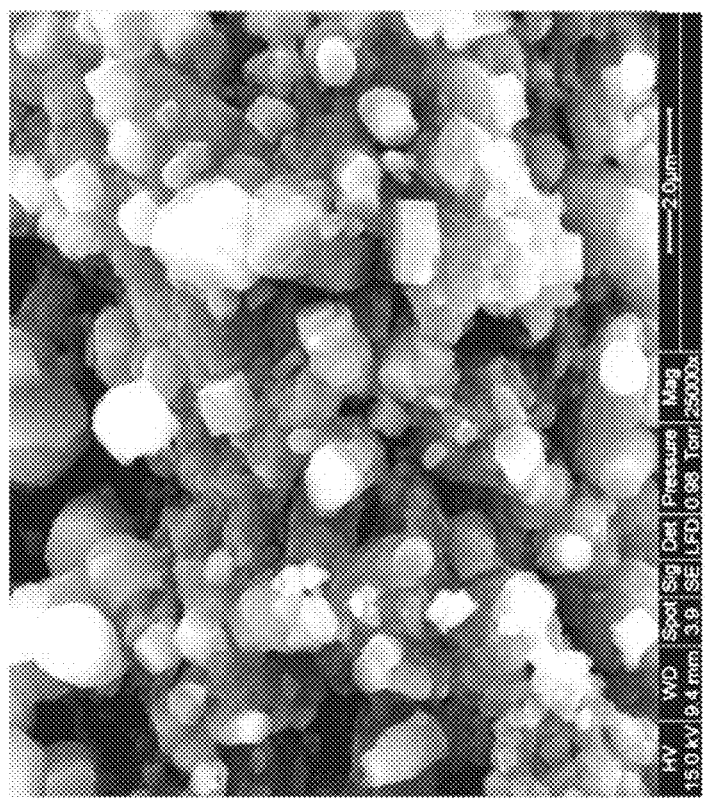
FIG. 4 illustrates photographs from scanning electron microscopy from (i) the external surface bearing the silver salt layer of an antimicrobial material having a titanium dioxide intermediate layer of 5 nm thickness (FIG. 4A) and (ii) the external surface of a comparative material having a titanium dioxide intermediate layer in hexagon aggregate shapes of 50-500 nm diameter (FIG. 4B).
Figure 4A:
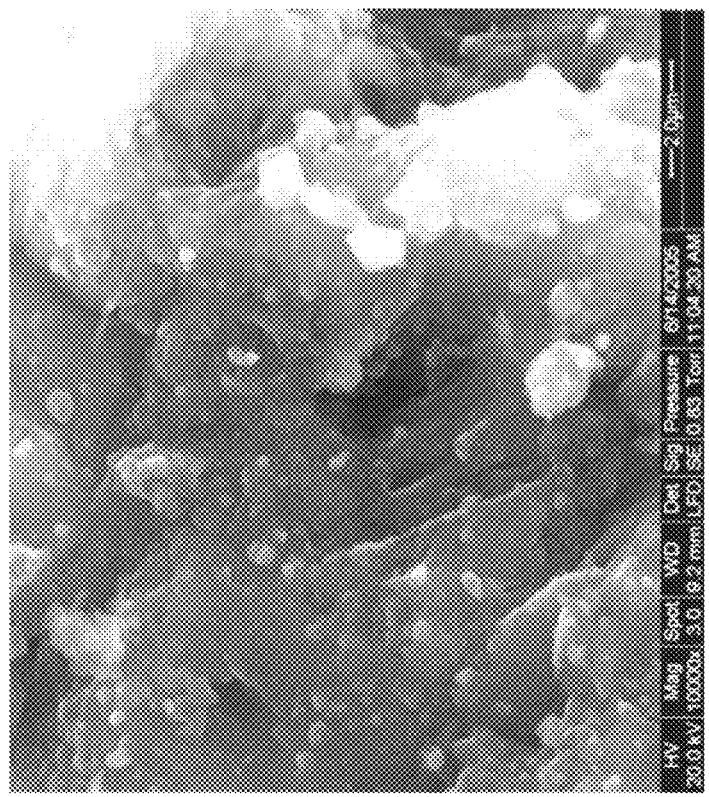
Figure 5:
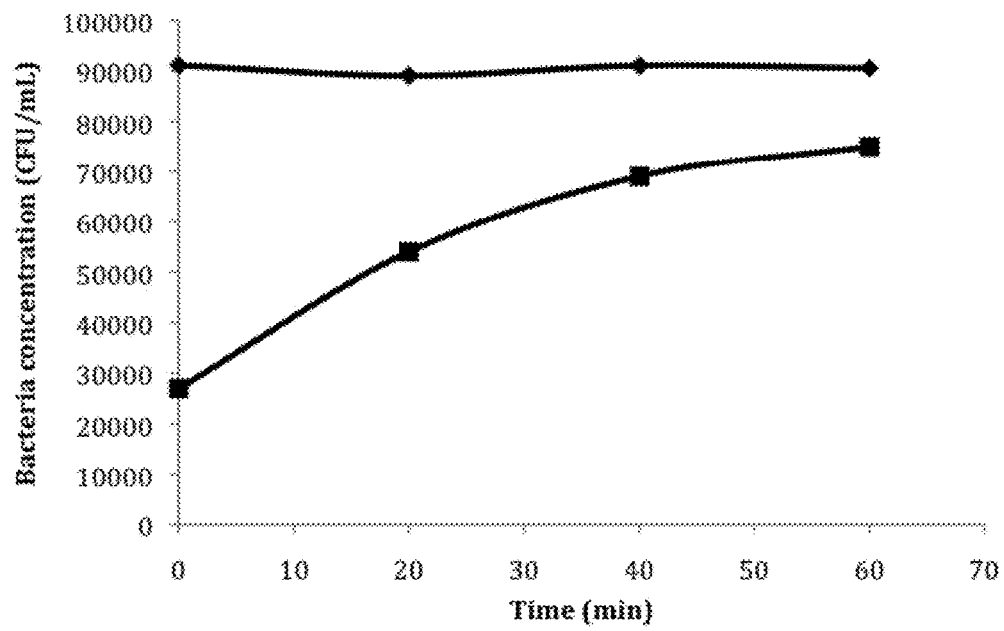
FIG. 5 illustrates the efficiency of a comparative material having a titanium dioxide intermediate layer in hexagon aggregate shapes of 50-500 nm diameter. Abscissa: time period of use expressed as the number of minutes. Ordinate: bacteria concentration expressed as CFU/mL. Upper curve with diamond symbols: concentration of bacteria in the fluid upstream the comparative material. Lower curve with square symbols: concentration of bacteria in the fluid downstream the comparative material.
Figure 6:
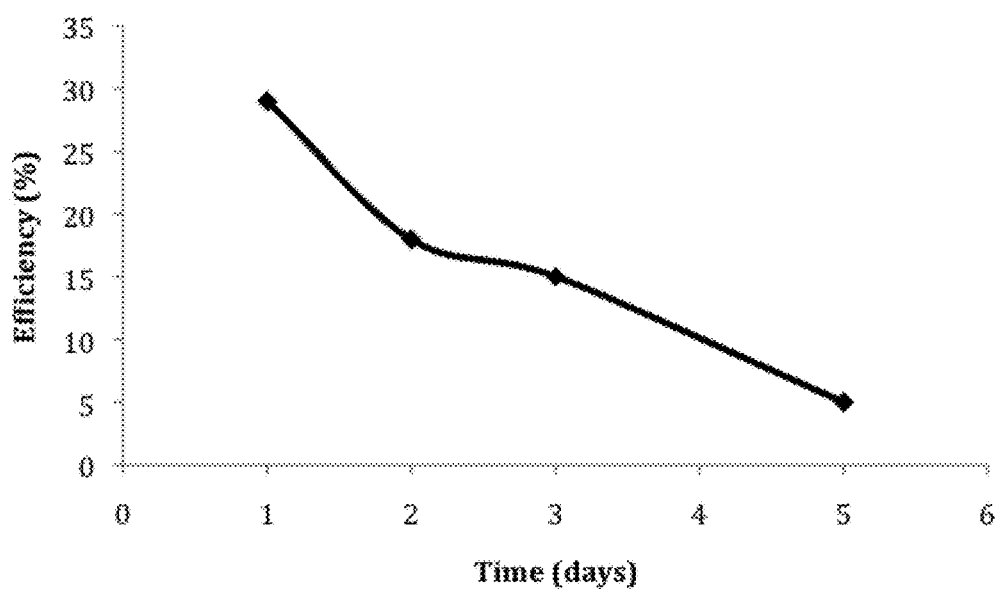
FIG. 6 illustrates the efficiency of a comparative material having a titanium dioxide intermediate layer in hexagon aggregate shapes of 50-500 nm diameter. Abscissa: time period of use expressed as the number of days. Ordinate: efficiency percentage as compared with an antimicrobial material having a titanium dioxide intermediate layer of 5 nm thickness.
Figure 7A:
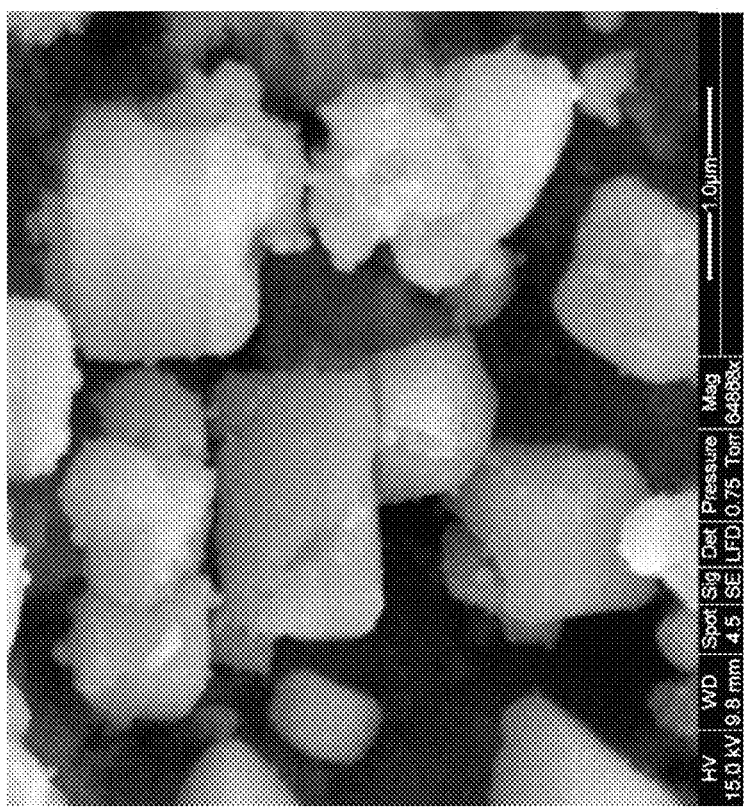
FIG. 7 illustrates photographs from scanning electron microscopy from (i) the external surface bearing the silver salt layer of an antimicrobial material (FIG. 7A) and (ii) the external surface of the same antimicrobial material after conversion of the salt layer particles into elemental silver (FIG. 7B).
Figure 7B:
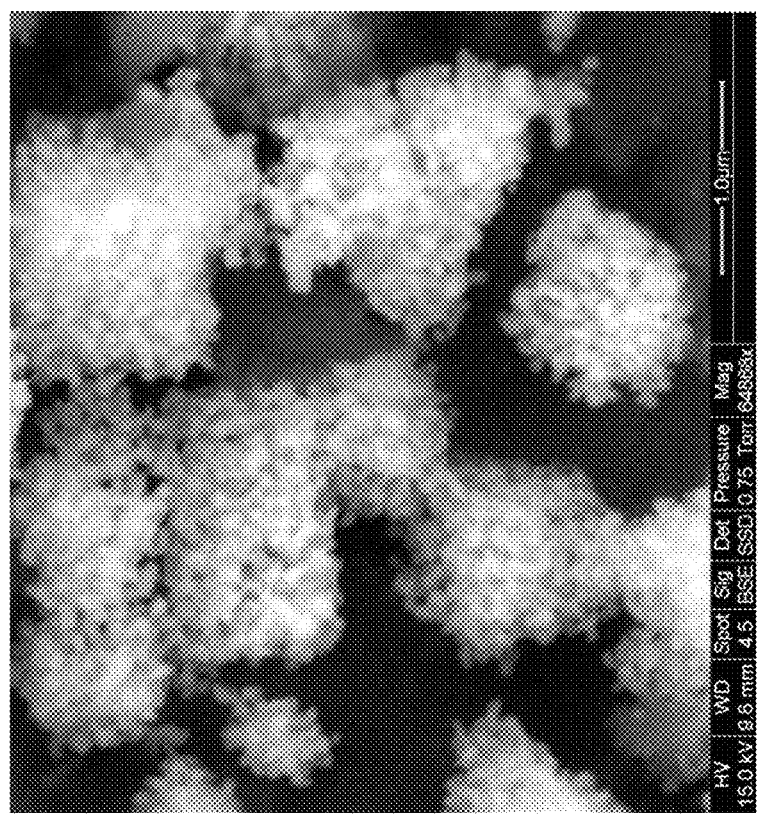
Figure 8:
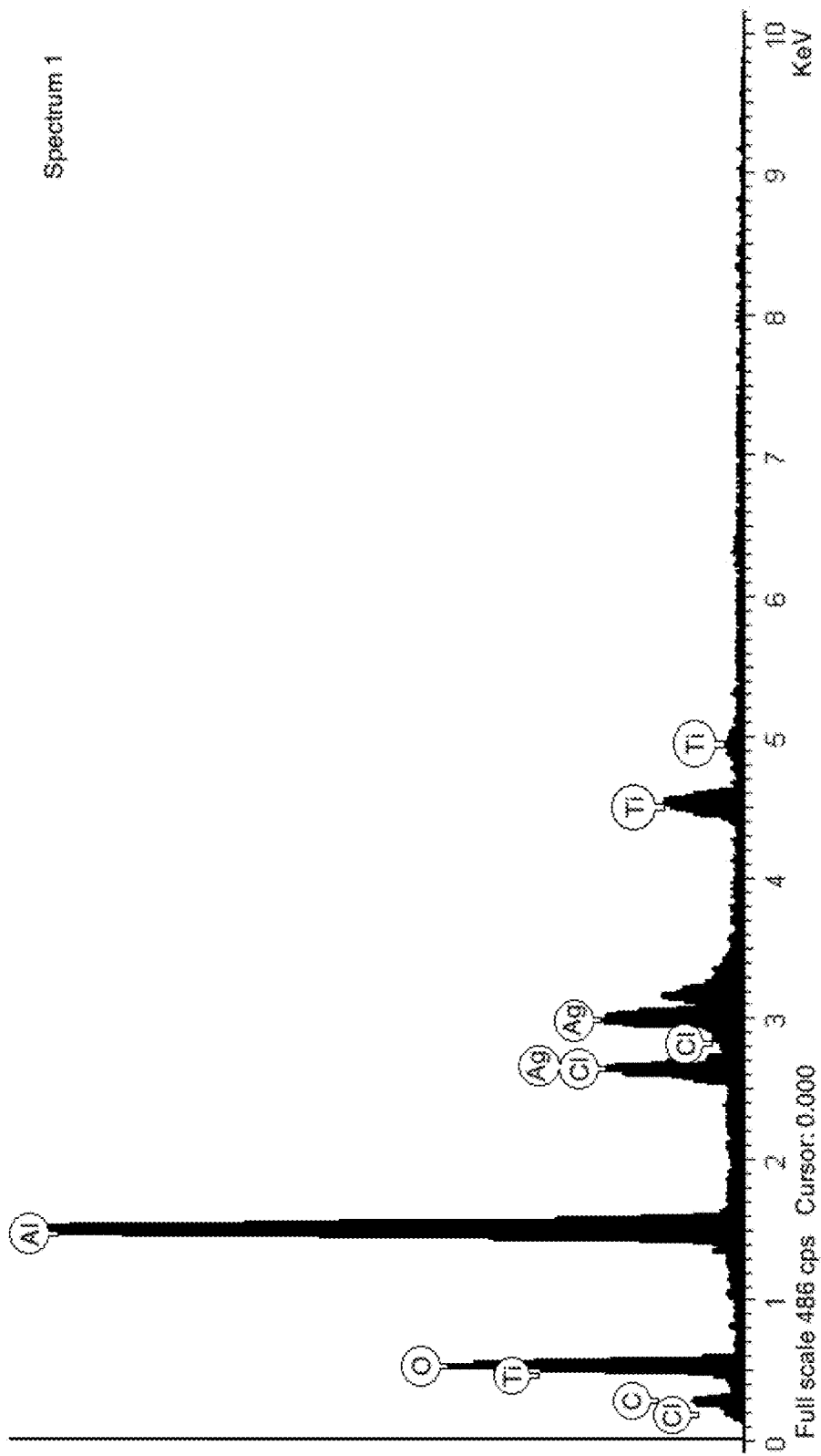
FIG. 8 illustrates an EDX spectrum (Energy Dispersive X-ray spectrum) of a sample of an antimicrobial material disclosed herein. Cl: chloride; C: carbon; Ti: titanium; O: oxygen; Ag: silver. Abscissa: X-ray energy, expressed as keV. Ordinate: level of the emission signal expressed as arbitrary units.
Figure 9A:
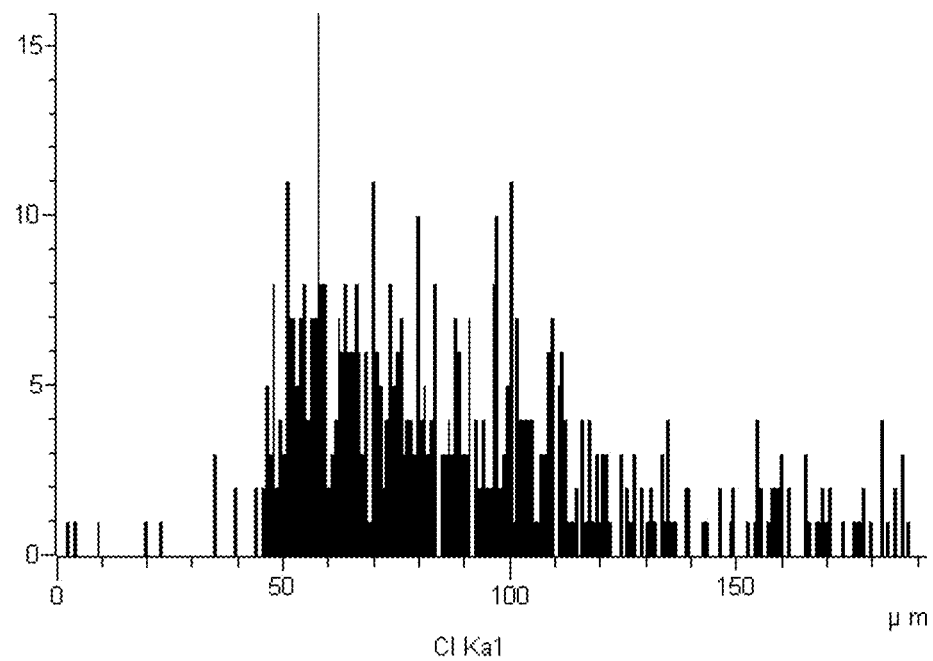
FIG. 9 illustrates the distribution of each of silver (FIG. 9A), chlorine (FIG. 9B) and titanium (FIG. 9C) as measured by EDX (Energy Dispersive X-Ray Spectrometry). Abscissa: level of the emission signal expressed as arbitrary units. Ordinate: distance from the external surface of the antimicrobial material disclosed herein expressed as micrometers (µm).
Figure 9B:
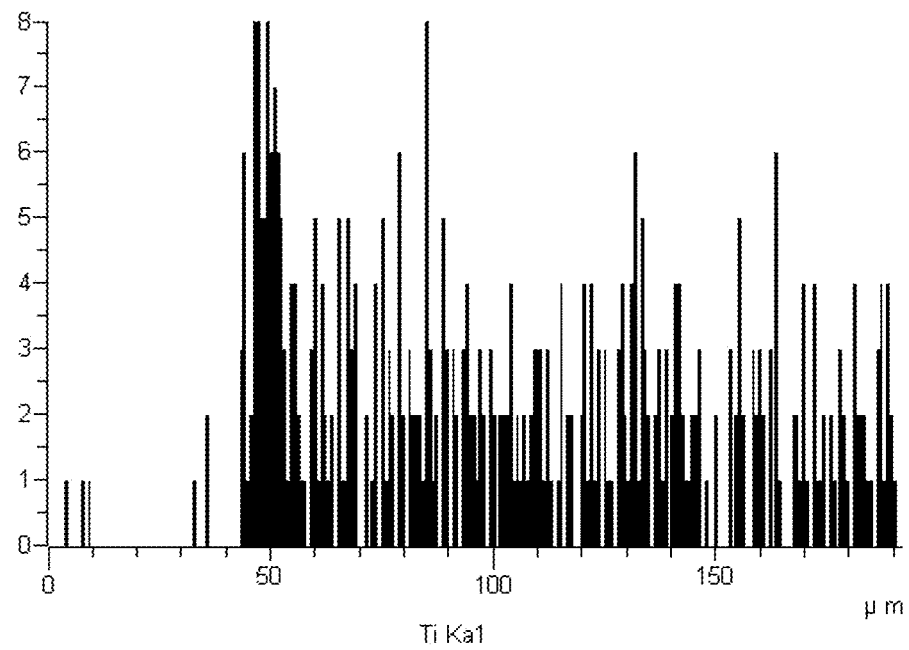
Figure 9C:
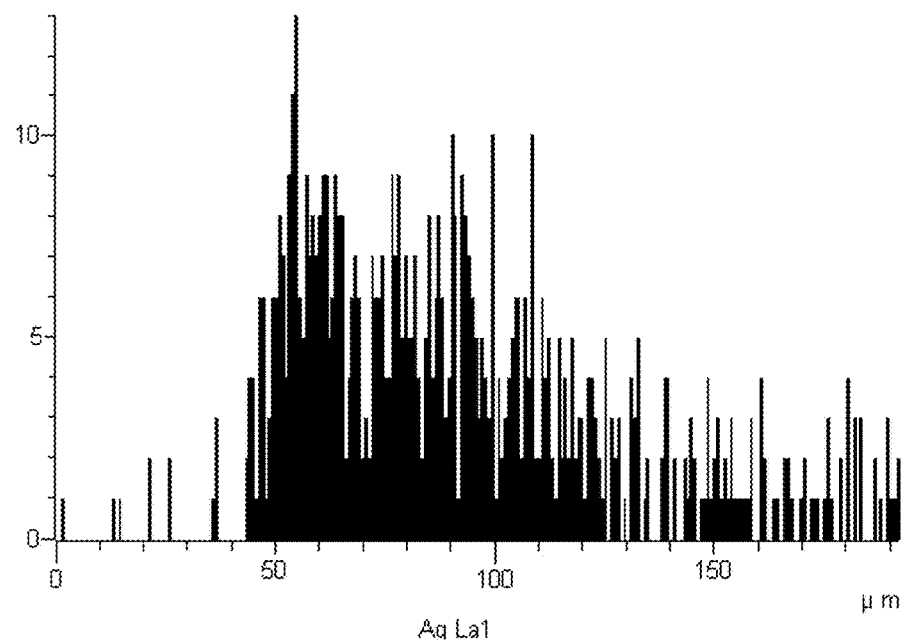

It is herein underlined that applying on the substrate a titanium dioxide layer of more than 50 nanometers also leads to the formation of titanium dioxide aggregates, which prevent the generation of a continuous and homogeneous titanium dioxide layer as a support for the silver salt layer. This is notably depicted in the appended FIG. 4.

According to the invention, a titanium dioxide layer having a thickness of less than 50 nanometers encompasses a titanium dioxide layer having a thickness of less than 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4 or 3 nanometers.

However, in preferred embodiments, the thickness of the titanium dioxide layer is of at least 3 nanometers, and most preferably of at least 5 nanometers, so as to ensure that the layer is continuous all over the surface portion of the porous activated ceramic substrate.

In some embodiments of an antimicrobial material according to the invention that are illustrated in the examples herein, the amount of titanium dioxide layer is less than 10% by weight, and most preferably around 5% by weight, based on the total weight of the antimicrobial material. In some embodiments, the titanium dioxide layer consists of a continuous layer that entirely covers the surface of the porous activated ceramic substrate.

As it is shown in the examples herein, the continuous titanium dioxide layer recovers the whole surface portion of the porous activated ceramic substrate, including the surface of the pores themselves. This is determined notably by the findings that (i) titanium atoms from the titanium dioxide layer and (ii) aluminium atoms from the porous activated ceramic substrate are found partly at the same depth inside the antimicrobial material according to the invention.

In preferred embodiments, the silver salt layer consists of a discontinuous layer where the silver salt does not recovers every surface location of the titanium dioxide layer, while the silver salt is homogeneously distributed on the whole surface area that is coated therewith.

In preferred embodiments, in the silver salt layer, the silver salt is covalently bonded to the titanium dioxide layer under the form of silver salt aggregates that are homogeneously dispersed on the whole titanium dioxide layer surface area. The presence of the silver salt as silver salt aggregates explains why the silver salt layer is termed, in these preferred embodiments, a discontinuous layer where the silver salt aggregates are not bonded to each and every location of the titanium dioxide layer.

As it has been already specified above, the silver salt layer preferably consists of a silver halide layer. Without wishing to be bound by any particular theory, the inventors believe that there is no doubt regarding the effectiveness of an antimicrobial material as disclosed herein having, as a silver salt layer, any kind of silver halide layer, since a full effectiveness of the antimicrobial material is shown in the examples using a specific silver halide layer, namely a chloride silver layer.

Thus, in some embodiments of the antimicrobial material of the invention, the silver salt layer consists of a silver halide layer selected from the group consisting of silver chloride, silver bromine, silver fluorine and silver iodide. A silver chloride layer is the most preferred silver salt layer.

As already specified in the present description, the silver salt covalently bound to the continuous layer of titanium dioxide.

As shown in the examples herein, the silver salt comprise various forms of silver including elemental silver (Ag), silver oxide (AgO) and silver salt (e.g. silver halide such as silver chloride—AgCl).

The results show that the silver salt layer comprises predominantly silver in the form of the silver salt (e.g. silver halide such as silver chloride—AgCl).

As it is also shown in the examples herein, the silver atoms and the titanium atoms are found at approximately the same depth in the final antimicrobial material, which means that the two layers are intimately bound one to the other. These results also show that almost all the silver salt is located at the external surface exposed to the environment of the antimicrobial material of the invention. These results further show that the silver salt is not in contact with the porous activated ceramic substrate, which means that the titanium dioxide layer actually forms a uniform and continuous coating over the whole coated surface portion of the porous activated ceramic material.

As it is also shown in the examples herein, and as already discussed previously herein, the silver salt layer does not form a continuous coating over the titanium dioxide layer. Rather, the silver salt layer is discontinuous, and preferably consists of aggregates, e.g. square nano-aggregates, which induces that part of the surface of the titanium dioxide layer is exposed to the environment, i.e. is exposed to the aqueous fluid to be treated upon use of the antimicrobial material of the invention.

In preferred embodiments, the thickness of the silver salt layer, preferably of the discontinuous silver salt layer, is of 50 nanometers or more.

In preferred embodiments, the thickness of the silver salt layer is of 500 nanometers or less.

If the thickness of the silver salt layer is of less than 50 nanometers, then the amount of silver salt is insufficient for obtaining a final product having the required antimicrobial activity.

If the thickness of the silver salt layer is of more than 500 nanometers, then the final product contains an unstable silver salt layer wherein the silver salt is heterogeneously distributed at the surface of the titanium dioxide layer.

In the silver salt layer, the silver salt aggregates, which may be also termed nano-aggregates herein, may have various shapes including square shape or hexagon shape as shown in the examples.

In some embodiments of an antimicrobial material according to the invention that are illustrated in the examples, the amount of silver salt layer is less than 10% by weight, and most preferably less than 5% by weight, based on the total weight of the antimicrobial material.

Owing to the specific combination of features of the antimicrobial material according to the invention, the external coated surface which is exposed to the environment contains silver under a cationic form, which is the known broad spectrum antimicrobial form of silver.

Importantly, it has been determined that silver remains predominantly under a cationic silver form, even after a long time period of using the antimicrobial material disclosed herein for decontaminating fluids, e.g. microorganisms-containing aqueous media, including microorganisms-containing water. Without wishing to be bound by any particular theory, the inventors believe that the permanent presence of silver in its cationic form at the surface of the antimicrobial material is due to the generation of a permanent electronic discharge of silver that is caused by the covalent bonding of the silver atoms to the titanium dioxide layer. Accordingly, it is believed that the Ti4+ cation that is present in the titanium dioxide layer attracts electrons from silver, which induces generation of silver in its cationic form. Then, the electrons originating from the silver layer and at least partly stored in the titanium dioxide layer are released in the external environment through the generation of extremely low electric currents. The electron excess stored within the titanium dioxide layer can be released in the external environment at surface locations of the antimicrobial material of the invention where the titanium dioxide layer is not covered by silver salt, and is thus exposed to the environment.

Thus, the present invention provides an antimicrobial material endowed with a permanent antimicrobial activity and which does not require to be regenerated after time periods of use. Rather, as it has been explained above, the antimicrobial material according to the invention continuously self-regenerates, since the continuous release of the excess electrons that have accumulated in the titanium dioxide layer permits to ensure a permanent electronic discharge of the silver salt layer, i.e. the permanent presence of an amount of cationic silver at the surface of the antimicrobial material effective for killing microorganisms, if those are present in the fluid to be treated.

In some embodiments, the cationic state of the external surface of an antimicrobial material of the invention, as expressed as the surface electronic discharge, may range from $10^{10}$ to $10^{12}$ electrons per $\mu m^2$ of surface area, e.g. from $5 \times 10^{10}$ to $5 \times 10^{11}$ electrons per $\mu m^2$ of surface area, which includes from $1 \times 10^9$ to $5 \times 10^9$ electrons per $\mu m^2$ of surface area.

It has been shown in the examples that illustrative embodiments of an antimicrobial material according to the invention possess a cationic state of about $2 \times 10^9$ lack of electrons per pmt of surface area.

According to the invention, the cationic state of the antimicrobial material is measured by determining, for a given surface area, the number of electrons which are required to convert all the silver atoms exposed in the given surface area into elemental silver (Ag), as it is illustrated in the examples herein.

The present invention also deals with a method for preparing an antimicrobial material comprising the steps of: a) providing a porous activated ceramic substrate; b) reacting the surface area of the porous activated ceramic substrate with titanium dioxide, so as to obtain a titanium dioxide-coated solid ceramic substrate; and c) depositing a silver salt layer on the titanium dioxide-coated porous activated ceramic substrate obtained at step b), so as to obtain the antimicrobial solid material.

At step b), reacting the surface area of the porous activated ceramic substrate with titanium dioxide may be performed following various methods that are known per se in the art, such as Chemical Vapour Deposition (CVD), Sol-gel deposition, Arc Ion Plating, Dip-Coating, Photo-Inducted Sol-Gel, Plasma Associated Metallo-Organic CVD, Sputtering and Laser Photo-Induced CVD.

Illustratively, Example 1 discloses an embodiment of the method above, wherein step b) is carried out by performing Chemical Vapour Deposition.

For performing step b) of the method, the titanium dioxide layer is most preferably obtained by using titanium tetrachloride (TiCl4) as the starting reagent, so as to generate a titanium-based precursor layer having TiOH—Cl entities exposed thereon. The presence of TiOH—Cl entities exposed on the titanium-based precursor layer facilitates the further generation of the silver salt layer, at step c) of the method.

At step c), depositing a silver salt layer on the titanium dioxide-coated porous activated ceramic substrate obtained at step b) may be performed by using various methods that are well known in the art.

Illustratively, Example 1 discloses an embodiment of the method above, wherein step c) is carried out by performing a method of dry impregnation.

For performing step c), silver nitrate (AgNO3) may be used as the starting reagent.

The present invention also pertains to a method for reducing or eliminating microorganisms from a fluid susceptible to contain microorganisms, comprising a step of bringing into contact the fluid with an antimicrobial material as disclosed throughout the instant specification.

In some embodiments, the microorganisms are selected from the group consisting of Gram+ and Gram− bacteria, spore and non-spore forming bacteria, vegetative and non-vegetative fungi, yeast, protozoa, micro-algae, viruses and any combination thereof.

The antimicrobial material according to the invention may be used in any suitable fluid treatment device, which includes waste water treatment plants, drinking water treatment apparatuses, domestic and industrial water treatment devices, water pools water treatment systems, air conditioning systems, and microbiological air treatment equipment. The antimicrobial material may also be used in rain water collection and purification systems.

Illustrative embodiments of use of an antimicrobial material according to the invention, particularly for water treatment, i.e. water pool water treatment, and air conditioning systems are disclosed in the examples herein.

Generally, the antimicrobial material according to the invention is placed in an adapted system so as to be brought into contact with the fluid to be treated in an optimized way allowing an efficient killing of the microorganisms susceptible to be contained in the fluid.

Generally, the treatment system is conceived so as to allow a contact of the whole volume of the fluid to be treated with the antimicrobial material of the invention.

Figure 11:
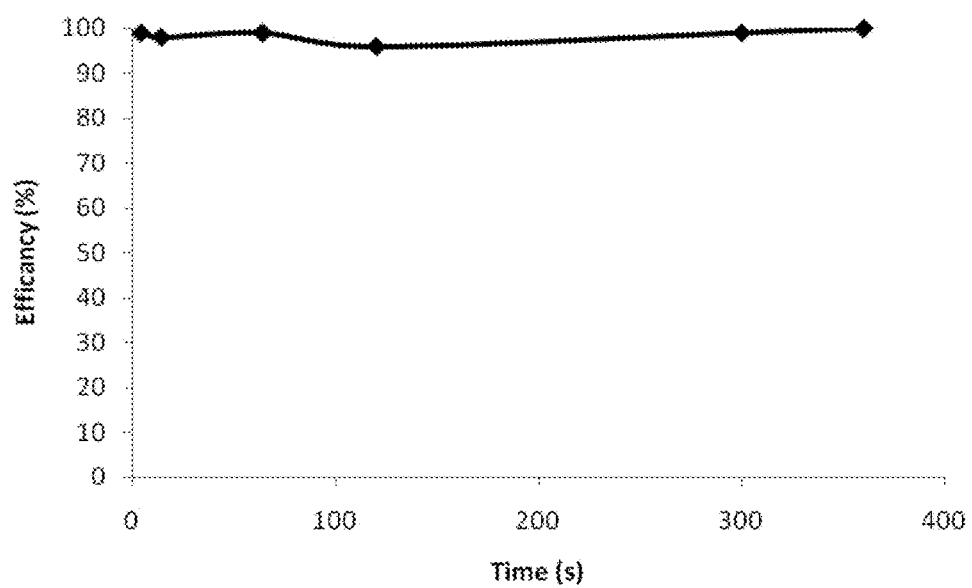
FIG. 11 illustrates the efficiency of an antimicrobial material disclosed herein at different contact times. Abscissa: time period of use expressed in seconds. Ordinate: efficiency of the antimicrobial material expressed as the percentage of bacteria initially present that are killed. The initial concentration of bacteria in test solutions was around 15,000 CFU/mL. The experiment contains an additional point, at 86,400 with an efficiency of 99.6% that, for visualisation reasons (not shown in FIG. 11).

As it is shown by the results of FIG. 11, the duration of the contact of the microorganisms with the antimicrobial material according to the invention does not influence its antimicrobial efficiency.

The results of FIG. 11 show that the antimicrobial material of the invention exerts almost the same biocidal activity when the fluid to be treated containing microorganisms is brought into contact therewith during either 86.400 seconds, 360 seconds, 300 seconds, 120 seconds, 64 seconds, 14 seconds. These results show that the microorganisms that are contained in a fluid are killed almost immediately, i.e. already after only several seconds of contact with the antimicrobial material according to the invention.

In all cases, the specific features of the treatment system may be easily adapted by the one skilled in the art, including for example the flow rate of the fluid to be treated through the decontaminating means wherein the antimicrobial material of the invention is confined.

Generally, the antimicrobial material of the invention is disposed in a decontaminating means so as to maximize the contact surface of the material with the fluid to be treated. In some embodiments, maximizing the contact surface may be reached by using small volume granulates of the antimicrobial material according to the invention. In some other embodiments, maximizing the contact surface may be reached by using a blade-shaped antimicrobial material according to the invention that is disposed in an appropriately dimensioned decontaminating means wherein the fluid to be treated circulates as a thin fluid layer over the whole surface of the antimicrobial material, from the fluid inlet means and towards the fluid outlet means of the decontaminating means.

The instant invention concerns an antimicrobial device comprising a decontamination vessel comprising an antimicrobial material according to the invention which is confined therein. Indeed, the one skilled in the art will easily adapt the way the antimicrobial material is confined within the decontamination vessel.

As used herein, a decontamination vessel may have various natures and shapes. In some embodiments, the decontamination vessel possess walls which are impermeable to fluids and possess fluid inlet means and fluid outlet means for allowing a circulation of the fluid to be treated inside the decontamination vessel. In other embodiments, the decontamination fluid is conceived with the sole aim of retaining the antimicrobial material therein and possesses walls which are permeable to fluids, so that the fluid to be treated is passively in contact with the antimicrobial material that is confined in the vessel. In the latter embodiment, the decontamination vessel may consist of a housing made of a fluid permeable fabric, e.g. a net fabric.

The instant invention also concerns an antimicrobial device comprising: a) means for circulating a fluid to be decontaminated, the means comprising (i) fluid inlet means, (ii) a decontaminating vessel and (iii) fluid outlet means, wherein the inlet means are in fluid communication with the decontaminating vessel and wherein the decontaminating vessel is in fluid communication with the fluid outlet means; b) an effective amount of an antimicrobial material that is disclosed herein that is confined in the decontaminating vessel.

Generally, the antimicrobial device above also comprises means suitable for confining the antimicrobial material in the decontaminating vessel, so as to avoid release of part of the antimicrobial material in the fluid which is treated.

In some embodiments, the device may comprise a packed granulate bed of the antimicrobial material according to the invention. In some embodiments, the device may include a housing for the packed granulate bed having an inlet and an outlet with the packed granulate bed disposed in-between. In some embodiments, the packed granulate bed may further comprise a porous medium at the inlet and outlet to confine the antimicrobial material according to the invention within the device housing. Suitable housings, inlet means, outlet means, and porous media for such packed granulate beds are well known to those of ordinary skill in the art. In some embodiments, the porous media may be a conventional filter media such as a porous polymeric media like polyethylene.

An antimicrobial material or device according to the invention may be used alone, or in combination with other materials and devices known in the art of fluid treatment. For instance, the antimicrobial material or device may be used in a process in series with a filtration device, for example as a pre-treatment to remove larger-scale particulate matter and/or as a post treatment to filter out skeletal remains of inactivated microorganisms.

The antimicrobial material according to the invention may be particularly useful in those applications where the required reduction in the concentration of microbiological contaminants significantly exceeds the regulatory standards for microbiological water purification devices. In one method of using such an antimicrobial material according to the invention, the microbiological contaminants are inactivated when the fluid is forced through the antimicrobial material by a difference in pressure on the influent and effluent sides or by a vacuum on the effluent side of the antimicrobial material.

The antimicrobial material according to the invention may be used as a purifier for drinking water. In another embodiment, the antimicrobial material may be used to purify water used in recreational settings, such as swimming pools, hot tubs, and spas. In such applications, the composite material may permit a reduction or elimination of chlorine usage, which is conventionally required to eliminate living microorganisms in such waters.

Because the antimicrobial material according to the invention efficiently inactivates microorganisms in aqueous solutions, it may also have numerous applications in the pharmaceutical, medical, food, or beverage industries manufacturing processes, fish farming, aquaculture, livestock farming and agriculture. It may, for example, be used for low-temperature sterilization, eliminating the need for techniques requiring elevated temperatures and pressures, such as pasteurization. It may also be used in industrial oil-treatment plants for oil industry.

Generally, the antimicrobial material according to the invention may be used in any situation wherein the prevention of generation of microorganism biofilms is sought or required.

The antimicrobial material according to the invention may also be used for residential, collective and industrial air-purification. Such applications would be especially useful for individuals who suffer from heightened reactivity to air-borne microorganisms, such as fungi. In another embodiment, the antimicrobial composite material may be used to protect individuals from air-borne microorganisms in the event of a bioterrorist attack.

In one particular application, the antimicrobial material according to the invention may be incorporated into a device designed to eliminate pathogenic protozoa (e.g., of the genus *Plasmodium* and *Phylum apicomplexa*) that cause diseases such as malaria. Malaria is typically transmitted to humans through mosquitoes, which become infected with the protozoa from water reservoirs and lakes where the mosquitoes breed. The present antimicrobial material may be used to assist in eliminating the protozoa from the breeding habitats of the mosquitoes, which could aid in eliminating malaria outbreaks.

Numerous other applications exist for which the present antimicrobial material can be used. Representative examples include the treatment of water used in cooling systems, fermentation applications and cell culture.

In each of these applications, the method of using the present antimicrobial material according to the invention is relatively simple: the fluid to be treated is brought into physical contact with the antimicrobial material of the invention. Typically, the fluid may be forced from one side of the composite material through pores in/among the antimicrobial material to the other side of the material due to gravity or a pressure drop across it. A conventional fluid pump or gravity feed can be used to drive the fluid contact.

The materials, devices, and methods described above will be further understood with reference to the following non-limiting examples.

EXAMPLES

Example 1

Method for Manufacturing an Antimicrobial Material

A. The Preparation of the Antimicrobial Material According to the Invention

The method for preparing an antimicrobial material according to the invention comprises the steps of: a) providing a porous activated ceramic substrate; b) reacting the surface area of the porous activated ceramic substrate with titanium dioxide, so as to obtain a titanium dioxide-coated solid ceramic substrate; and c) depositing a silver salt layer in shapes of aggregates on the titanium dioxide-coated porous activated ceramic substrate obtained at step b), so as to obtain the antimicrobial solid material.

As porous activated ceramic substrate is used an γ activated alumina (γ-Al2O3) with the following characteristics (Axens, France) shown in Table 1 below.

TABLE 1

| Characteristic | Value |
| --- | --- |
| Commercial name | SPH 538$^F$ |
| Physical state | solid |
| Shape | trilobed extruded cylinders |
| Aggregate dimensions: diameter × lengthiness (mm) | 1.6 × 5 – 10 |
| Colour | white |
| Fusion temperature (° C.) | >2000 |
| Commercial name | SPH 538$^F$ |
| Physical state | solid |
| Apparent density (g/cm$^3$) | 591 |
| Density, $\Omega_{37\ A} \cdot 10^3$ (g/cm$^3$) | ~0.68 |
| Specific aria (m$^2$/g) | 269-273 |
| Loss-on-Ignition at 1,000° C. (%) | 4.1 |
| Pore volume (cm$^3$/100 g) | 71.3 |
| Pore diameter (nm) | ~12 |
| Crashing grain by grain (daN/mm) | 2.1 |
| Na content expressed in Na$_2$O (ppm) | 647 |
| Water adsorption capacity (mass %) | ~40 |

The step b) is carried out following the Chemical Vapour Deposition method disclosed by Malygin A. A. in his article "The molecular layering method as a basis of chemical nanotechnology" (1999, In Book: Natural Microporous Materials in Environmental Technology: Kluwer Academic Publishers, 487-495).

1,000 g of γ-Al2O3 is modified with TiO2 coating into a vertical glace reactor according to the 3 steps presented by Malygin:

1. Conditioning: the reactor is heated at 230-350° C. when dry air is passing by with a flow speed around 5 L/min during 3 hours;

2. Synthesis: in order to generate a titanium-based precursor layer having TiOH—Cl entities exposed thereon, the titanium dioxide layer was obtained by using titanium tetrachloride (TiCl4) as the starting reagent. The γ-Al2O3 is exposed to a TiCl4 flow (1 L/min) during 16 hours;

3. Hydrolysis: in order to eliminate superficial chloride molecules and to complete the TiO2 growth, the activated alumina surface was sweep with humid air (RH=100%, rate flow=1 l/min) during 10 hours.

After cooling the sample is ready for the step c).

At step c), depositing a silver salt layer on the titanium dioxide-coated porous activated ceramic substrate obtained at step b) is carried out by performing the dry impregnation method.

For performing step c), silver nitrate (AgNO3) is used as the starting reagent. The titanium dioxide-coated porous activated ceramic substrate obtained at step b) is soaked with 1 L of silver nitrate solution (concentration: 0.1 M), marinated for 4 hours and then dry at 105° C. during 4 hours. Afterword, the silver impregnated titanium dioxide-coated porous activated ceramic substrate is calcined at 400-550° C. during 4 hours.

B. The Preparation of the Antimicrobial Material Based on Polymer Support

The antimicrobial material based on polymer support is prepared according to the same stapes as described for the preparation of the antimicrobial material according to the invention.

The chosen polymer support is an ordinary polyethylene in shapes of small square strips (10×10×1 mm).

Table 2 below regroups the steps and the operational parameters of the elaboration method of the antimicrobial material based on polymer support.

TABLE 2

| No. | Step | Time (hours) | Temperature (° C.) | Flow rate (L/min) |
|---|---|---|---|---|
| 1 | TiO$_2$ Conditioning | 3 | 70 | 5 |
| 2 | TiO$_2$ Synthesis | 16 | 70 | 1 |
| 3 | TiO$_2$ Hydrolysis | 10 | 70 | 1 |
| 4 | Marinating in AgNO$_3$ solution | 4 | 22 | — |
| 5 | Drying | 4 | 50 | 5 |
| 1 | TiO$_2$ Conditioning | 3 | 70 | 5 |
| 2 | TiO$_2$ Synthesis | 16 | 70 | 1 |
| 6 | Calcination | 2 | 80 | 1 |

C. The Preparation of the Antimicrobial Material Containing 2 Layers of Titanium Dioxide Coating Over the Porous Ceramic Support The antimicrobial material containing 2 layers of titanium dioxide coating over the porous ceramic support is prepared according to the same stapes as described for the preparation of the antimicrobial material according to the invention, only that the titanium oxide coating is made in 2 consecutives cycles.

Table 3 regroups the steps and the operational parameters of the elaboration method of the antimicrobial material containing 2 layers of titanium dioxide coating.

TABLE 3

| No. | Step | Time (hours) | Temperature (° C.) | Flow rate (L/min) |
|---|---|---|---|---|
| 1 | 1$^{st}$ layer TiO$_2$ Conditioning | 3 | 230-350 | 5 |
| 2 | 1$^{st}$ layer TiO$_2$ Synthesis | 16 | 230-350 | 1 |
| 3 | 1$^{st}$ layer TiO$_2$ Hydrolysis | 10 | 230-350 | 1 |
|  | 2$^{nd}$ layer TiO$_2$ Conditioning | 3 | 230-350 | 5 |
|  | 2$^{nd}$ layer TiO$_2$ Synthesis | 16 | 230-350 | 1 |
|  | 2$^{nd}$ layer TiO$_2$ Hydrolysis | 10 | 230-350 | 1 |
| 4 | Marinating in AgNO$_3$ solution | 4 | 22 | — |
| 5 | Drying | 4 | 105 | — |
| 6 | Calcination | 4 | 400-550 | 1 |

The characteristics of the samples elaborated according to the descriptions presented at A, B and C are regrouped in the following table 4.

TABLE 4

| Step | Antimicrobial material according with the invention | Antimicrobial material elaborated on polymer support | Antimicrobial material coated with 2 TiO$_2$ layers |
|---|---|---|---|
| Sample quantity (kg) | 1 | 1 | 1 |
| TiO$_2$ layer size (nm) | 5-8 | >1 | 50-300 |
| TiO$_2$ layer shape | continuous layer | discontinuous layer | layer and aggregates |
| TiO$_2$ content (% mass) | 6.3 | 0.3 | 11.4 |
| Specific aria (m$^2$/g) | 230-250 | 10-20 | 190-210 |
| AgCl layer size (nm) | 50-500 | 5-50 | 500-1000 |
| AgCl layer shape | square aggregates | square aggregates | particle agglomerates |
| Quantity of AgCl aggregates/5 µm$^2$ | ~30 | 1 | 5 |

Example 2

Use of an Antimicrobial Material for Water Treatment (Laboratory Scale)

A. Materials and Methods

Bacteria used for the assay were from the E. coli strain PVC18 AMP (Institut National de la Recherche Agronomique (INRA), France).

Bacterial stock suspensions were prepared by diluting 10 µL of the starting bacterial liquid suspension in 10 mL of Broth High Slat culture medium—LB (Fulka, France).

A 20 hours incubation time period at 37° C. of the bacterial stock suspensions has allowed the growth of a reproducible number of bacteria which was of about 18.106 CFU (Colony Forming Units). Each of these bacterial stock suspensions was then used for a maximum of three consecutive experiments (three consecutive days).

For performing the experiment, two containers, respectively a feeding container A and a recipient container B (5 L of volume), were placed in fluid communication through a pipe. A pump was interposed between containers A and B for transferring the fluid (5 L liquid) from the feeding container A to the recipient container B. The pump used had a maximum flow rate capacity of 9 L/min (Heidolph Pumpdrive 5201 SP Quick, AcrosOrganics, France). A glass cylindrical vessel containing an antimicrobial material prepared according to Example 1 has been placed in the fluid circuit between the pump and the recipient container B. The probes of two pH meter devices were placed in the feeding container A and in the recipient container B respectively, for continuous measurement of the pH of the liquid solutions contained in each container. The solutions contained in containers A and B were continuously homogenized my magnetic stirring means.

For the experiment, the feeding container A was inoculated with the desired volume of a bacterial stock solution and the pump is started at a flow rate of 120 mL/min.

5 mL samples were collected at 15-20 minutes intervals simultaneously in both containers A and B. The experiment was continued during one hour.

25 µL of each of the collected samples were seeded in Petri dishes containing nutritive LB—Agar Broth High Slat (Fulka, France). Then, the Petri dishes were incubated at 37° C. during 16 hours and the number of CFU per Petri dish was then determined.

B. Results

For showing the biocidal activity of the antimicrobial material according to Example 1, 12 distinct assays were performed during a period of time of 40 days using the same operating conditions. The pH measurements shown that the test solutions remain stable, around 7, during the all test period.

The sole variable parameter was the starting bacterial concentration. The results are presented in Table 5 below.

TABLE 5

| Number of days following manufacture | Mean number of bacteria upstream the glass vessel | Efficiency | |
|---|---|---|---|
| | | Number of killed bacteria (CFU) | (%) |
| 3 | 473 | 460 | 97 |
| 4 | 10528 | 10488 | 99 |
| 6 | 31590 | 31450 | 100 |
| 7 | 1880000 | 1316000 | 70 |
| 8 | 1198500 | 685500 | 58 |
| 9 | 45710 | 41340 | 89 |

TABLE 5-continued

| Number of days following manufacture | Mean number of bacteria upstream the glass vessel | Efficiency | |
|---|---|---|---|
| | | Number of killed bacteria (CFU) | (%) |
| 11 | 7920 | 7366 | 85 |
| 12 | 6826 | 6393 | 94 |
| 14 | 1717000 | 838500 | 49 |
| 16 | 52433 | 44840 | 86 |
| 28 | 6280 | 6280 | 100 |
| 39 | 1303000 | 919500 | 71 |

The results of Table 5 show the high and long term biocidal activity of the antimicrobial material prepared according to Example 1.

Figure 10:
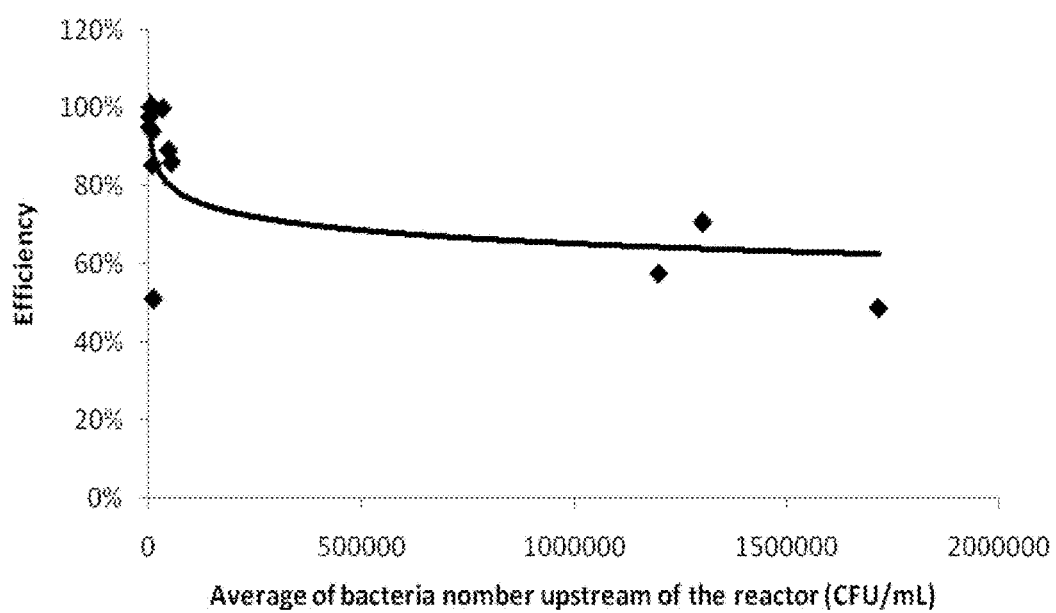
FIG. 10 illustrates the efficiency of an antimicrobial material disclosed herein. Abscissa: mean number of bacteria upstream the reactor containing the antimicrobial bacterial expressed in CFU/mL. Ordinate: efficiency of the antimicrobial material expressed as the percentage of bacteria initially present that are killed.

Further, starting from the results of Table 5, FIG. 10 shows a curve illustrating the efficiency of the antimicrobial material in relation to the mean number of bacteria present in the feeding container A for each assay. The results of FIG. 10 demonstrate that the biocidal efficiency of the antimicrobial material increases with a decreased number of bacteria present in the starting bacterial suspension, irrespective of the day following the manufacture of the antimicrobial material upon which the experiment was performed.

These results show that the antimicrobial material has undergone no measurable loss of efficiency with time.

Example 3

Use of an Antimicrobial Material for Water Treatment (Industrial Scale)

A. Materials and Methods

The water recycling systems of three distinct swimming pools were equipped with filters containing an antimicrobial material prepared as disclosed in Example 1.

The monitoring of the bacterial concentration evolution in the pool water was performed by using the Colilert-18 test kit (Indexx, France).

The operating conditions are summarized in Table 6 below.

TABLE 6

| SP Ref | Basin volume | Filter type | Loss of charge (%) | Amount of antimicrobial material (kg) | Flow rate (m³/h) |
|---|---|---|---|---|---|
| 1P | 90 | Send filter | 30 | 3 | 22 |
| 2D | 60 | Send filter | 1-2 | 2 | 15 |
| 3R | 30 | Send filter | 0 | 1.5 | 8 |

B. Results

The results are presented in Table 7 below.

TABLE 7

| SP Ref | Day of sampling (results expressed as bacterial concentration in CFU/mL) | | | | | | | | | | | | | | | | | | | |
|---|---|---|---|---|---|---|---|---|---|---|---|---|---|---|---|---|---|---|---|---|
| | 0 | 1 | 3 | 7 | 12 | 17 | 25 | 27 | 34 | 37 | 40 | 47 | 54 | 58 | 63 | 69 | 74 | 84 | 93 | 103 |
| 1P | 60 | 0 | 0 | 0 | 0 | 0 | 0 | 0 | 34 | 50 | 0 | 0 | 0 | 0 | 0 | 0 | 0 | 0 | 0 | 0 |
| 2D | 0 | 0 | 0 | 0 | 0 | 0 | 0 | 0 | 0 | 0 | 0 | 10 | 0 | 0 | 0 | 0 | 0 | 0 | 0 | 0 |
| 3R | 0 | 0 | 0 | 0 | 10 | 0 | 0 | 0 | 0 | 0 | 0 | 0 | 0 | 0 | 0 | 0 | 0 | 0 | 0 | 0 |

It is herein noticed that the Swimming Pool no 1P was filled with a well-derived water containing bacteria at a concentration of about 60 CFU/mL. The swimming pools no 2D and 3R were filled with chloride-containing drinking water.

The results show that the antimicrobial material prepared as disclosed in Example 1 has retained its antimicrobial efficiency when used in real life operating conditions.

The results also show that, once the recycling system was equipped with a filter containing the antimicrobial material, absence of a measurable amount of bacterial cells in the pool water was determined.

The atypical results wherein a measurable amount of bacterial cells in the pool water was determined were explained by the occurrence of dysfunctions of the water recycling system.

Regarding the swimming pool no 1P, the recycling pump was stopped on days 30 to 37.

Regarding the swimming pool no 3R, a substantial loss of charge (more than 80%) about 10 days following installation of the filter containing the antimicrobial material, due to a substantial pH variation of the pool water.

Example 4

Use of the Antimicrobial Material in Air Conditioning Equipment (Laboratory Scale)

Materials and Methods

For testing the biocidal capacity of the antimicrobial material of Example 1 for the purpose of sanitizing the condensation fluids produced by operating air conditioning systems, an experimental installation mimicking real scale medium size systems was designed by using a condensate recipient tub sizing 56×10 centimeters.

A sample of the antimicrobial material prepared according to Example 1 under the form of trilobed extruded cylinders (size of 1.6×10 cm) was stuck on both surfaces of a transparent polymethcrylate plate specifically sized for being introduced into the condensate recipient tub.

The designed experimental installation comprises a 5 L glass container containing the test bacterial suspension (*E. coli* as in Example 2) having an outlet means equipped with a tap allowing to control the flow rate. Homogenization of the bacterial suspension was ensured through a magnetic stirring device. The glass container was placed above the condensate recipient tub, so as to allow pouring the bacterial suspension over the tub at a desired flow rate.

The condensate recipient tub containing the antimicrobial material immobilized on the polymethacrylate plate may be oriented at the desired inclination angle of 5° with respect to the horizontal plane, so as to allow the flow of the bacterial suspension along a desired route length over the antimicrobial material contained in the condensate recipient tub. Route lengths of the bacterial suspension over the antimicrobial material of 10 cm, 25 cm and 44 cm were selected, respectively.

The control of the flow rate value has allowed selecting the duration of the stay of the bacterial suspension in contact with the antimicrobial material.

Additionally, the pH values of both, the upstream bacterial suspension and of the downstream fluid, were determined using pH meter devices (Eoscan pH 5/6, Acros Organics, France).

For each experiment, two 25 µL samples upstream and downstream the condensate recipient tub were performed at 15 minutes time intervals during a period of time of one hour. These samples were seeded on Petri dishes containing nutritive broth (LB medium in 25% w/w Agar). The Petri dishes were then incubated at 37° C. during 18 hours and the number of bacteria was determined by counting the number of CFU.

The operating conditions used are presented in Table 8 below.

TABLE 8

| Parameters | Value |
| --- | --- |
| Amount of antimicrobial material (g) | 55 |
| Water amount (L) | 5 |
| Size of the condensate recipient tub (L × l in cm) | 53 × 9.5 |
| Amount of liquid solution added to a Petri dish (µL) | 25 |
| Bacterial concentration (CFU/mL) | About 15000 |
| Test duration (min) | 60 |
| Temperature (° C.) | 20-23 |

The flow rates used for each route length of the bacterial suspension as well as the stay duration of the bacterial suspension over the antimicrobial material are presented in Table 9 below.

TABLE 9

Flow rates used for each position and corresponding stay durations for the test installation

| Parameter | Value | | | | | | | | | | | |
| --- | --- | --- | --- | --- | --- | --- | --- | --- | --- | --- | --- | --- |
| Position of the recipient containing the bacterial solution (FIG. 14) | 1 | | | | 2 | | | | 3 | | | |
| Route length of the bacterial solution over the product (cm) | 10 | | | | 25 | | | | 44 | | | |
| Flow rate of the bacterial solution (mL/min) | 11 | 24 | 28 | 46 | 14 | 24 | 31 | 40 | 8 | 17 | 30 | 37 |
| Stay duration of the solution over the surface of the product, (s) | 80 | 19 | 55 | 23 | 24 | 70 | 15 | 80 | 343 | 147 | 105 | 59 |

The flow rate of the bacterial suspension is inversely proportional to the stay duration (Ts) thereof in contact with the antimicrobial material. However the value of Ts may also vary with the moistening state of the antimicrobial material. This explained why the values recorded for the route lengths 1 and 2 in columns 2 and 7 of above Table 9 are not in the expected proportionality.

B. Results

The results illustrating the antimicrobial efficiency of the antimicrobial material are shown in Table 10 below for the various operating conditions used.

TABLE 10

Biocidal efficiency of the antimicrobial material

| Ts*(s) | Efficiency (%) | | | | | | | | | | | |
| --- | --- | --- | --- | --- | --- | --- | --- | --- | --- | --- | --- | --- |
| Position | 19 | 23 | 55 | 80 | 15 | 24 | 70 | 80 | 59 | 105 | 147 | 343 |
| 1 | 56 | 63 | 63 | 82 | | | | | | | | |
| 2 | | | | | 67 | 57 | 80 | — | | | | |
| 3 | | | | | | | | | 69 | 70 | 78 | 90 |
| MB** (CFU/mL) | 185.220 | 136.320 | 34.200 | 12.030 | 57.090 | 24.780 | 42.750 | — | 52.410 | 27.810 | 7.440 | 76.260 |

*Ts: Stay duration of the bacterial suspension over the nano-composite product
**MB: Average of the bacterial number in the solution test The results of Table 10 above demonstrate the biocidal efficiency of the antimicrobial material.

When further analysing the results by expressing the biocidal efficiency values in function of the route lengths of the bacterial suspension over the antimicrobial material, it has been further determined that the biocidal efficiency increased with an increasing duration of the time of the bacterial suspension in contact with the antimicrobial material.

The high biocidal efficiency is notably illustrated by the results herein which show that the antimicrobial material possesses a microorganism killing capacity ranging from 5803 to 103723 CFU/mL, depending of the assay considered.

This biocidal efficiency is largely sufficient for blocking bacterial development in the condensate recipients equipping air conditioning systems, where the bacterial provision is always lower than 1 CFU/mL (see BIOMEDD circular document no 06/3 dated of Feb. 15, 2006).

Example 5

Biocidal Spectrum of the Antimicrobial Material

The results of the above examples 2-4 have shown that the antimicrobial material prepared according to Example 1 possesses a biocidal efficiency which mat exceeds 99.9% against *E. coli.*

In this example, further assays have been performed for determining if the antimicrobial material prepared according to Example 1 has a broad spectrum of antimicrobial activity.

A. Materials and Methods

A.1. Evaluation of the Biocidal Activity Against Bacteria and Fungi

1. Description of the Assay

The material to be evaluated was the antimicrobial material prepared according to Example 1.

Two different types of assays have been performed: dynamic assay: the microorganisms suspension flows through a column containing the particles and stagnation assay: the microorganisms suspension is incubated with the particles without any agitation.

2. Calibration

Three microbial strains have been evaluated: a gram positive bacteria (*Staphylococcus aureus*), a gram negative bacteria (*Legionella adelaidensis* as a surrogate of *Legionella pneumophila*) and a yeast (*Candida albicans*).

The initial concentration of the microorganisms' suspension is of 100, 300 or 3000 CFU/mL of suspension. In a first attempt, it is necessary to evaluate the adsorption of the microorganisms to the untreated particles (negative control) in order to adjust the initial concentration if appropriate.

In addition, in order to improve the sensitivity of the assay, it may be profitable to centrifuge the sample. However, in some cases, the centrifugation may have a negative impact on the viability of the microorganisms.

The following experiment has been performed to evaluate the adsorption of the different microorganisms onto the untreated particles and to evaluate the interest of centrifugation.

For each strain, a suspension at 300 CFU/mL has been prepared. From each of these suspensions, four samples have been prepared:

1. the initial suspension at 300 CFU/mL with no additional treatment
2. the initial suspension at 300 CFU/mL concentrated 100 times by centrifugation
3. 50 mL of the suspension passed through 3 g of the untreated particles in 14 s
4. 50 mL of the suspension passed through 3 g of the untreated particles in 14 s and concentrated 100 times by centrifugation The recovered microorganisms have been quantified in these samples by culture of serial 1/3 dilutions of the samples.

For bacteria, in each well, growth has been detected using a colorimetric method: wells were growth occurred are coloured purple and wells were growth did not occur are coloured yellow. Since the detection is more sensitive for the naked eye than in images, for each sample, the last detected dilution has been determined. For *C. albicans*, the detection has been performed by OD measurement at 600 nanometers.

3. Efficiencies

The efficiency has been calculated as follows: when growth is detected in one well less than in controls, this means that viability is reduced by ⅓; when growth is detected in two wells less than in controls, this means that viability is reduced by ⅑.

For all the assays that are described here, the efficiency is superior to the measurable efficiency: no microbial growth is detected even in the undiluted sample (first well of the serial dilutions). The measurable efficiency varies from 32 to 36, depending on the concentration of the microorganisms in the negative controls (untreated porous inactivated ceramic); this corresponds to 88.89% to 98.86%.

A.2. Evaluation of the Biocidal Activity Against Microalgae

1. Calibration

The evaluated strain is a microalgae Anabaena constricta.

The initial concentration of the microorganisms' suspension is, as described in the protocol provided by the Client, 300 CFU/mL of suspension. In a first attempt, it is necessary to evaluate the adsorption of the microorganisms to the untreated particles (negative control) in order to adjust the initial concentration if appropriate.

In addition, in order to improve the sensitivity of the assay, it may be profitable to centrifuge the sample. However, in some cases, the centrifugation may have a negative impact on the viability of the microorganisms.

The following experiment has been performed to evaluate the adsorption of the microorganisms onto the untreated particles and to evaluate the interest of centrifugation.

A suspension at 300 CFU/mL has been prepared. From this suspension, four samples have been prepared:

1. the initial suspension at 300 CFU/mL with no additional treatment
2. the initial suspension at 300 CFU/mL concentrated 100 times by centrifugation
3. suspension passed through 3 g of the untreated particles (outflow of 3.5 mL/s)
4. suspension passed through 3 g of the untreated particles (outflow of 3.5 mL/s) and concentrated 100 times by centrifugation The recovered microorganisms have been quantified in these samples by culture of serial 1/3 dilutions of the samples.

In each well, growth has been detected by eye due to the green colour of the algae.

2. Efficiency

The efficiency has been calculated as follows: when growth is detected in one well less than in controls, this means that viability is reduced by ⅓; when growth is detected in two wells less than in controls, this means that viability is reduced by ⅑ . . . .

For all the assays that are described here, the efficiency is superior to the measurable efficiency: no microbial growth is detected even in the undiluted sample (first well of the serial dilutions). The measurable efficiency varies from 32 to 33, depending on the concentration of the microorganisms in the negative controls (untreated ceramic); this corresponds to 88.89% to 96.30%.

B. Results

The results of Table 11 below show that the antimicrobial material possesses the same high level biocidal efficiency against all the other microorganisms tested, namely, *Staphylococcus aureus*, *Legionella adelaidensis*, *Candida albicans*, and *Anabena constricta*.

TABLE 11

Biocidal efficiency of the nano-composite product with ceramic base

| Microorganism (MO) | Type of MO | Antimicrobial efficiency (%) |
|---|---|---|
| *Staphylococcus aureus* | Bacteria | 98.77 |
| *Legionella Adelaidensis* | Bacteria | 99.77 |
| *Candida albicans* | Yeast | 95.75 |
| *Anabaena constricta* | Algae | 96.55 |

What is claimed is:

1. An antimicrobial material comprising:
   a porous activated ceramic substrate;
   a titanium dioxide layer covalently bound to the ceramic substrate wherein the titanium dioxide layer is a continuous layer covering the entire surface of the porous activated ceramic substrate; and
   a silver salt layer covalently bound to the titanium dioxide layer wherein the silver salt layer forms a discontinuous coating over the titanium dioxide layer, wherein the silver salt layer generates a permanent electronic discharge while remaining covalently bound to the titanium dioxide layer;
   wherein the titanium dioxide layer has a thickness of less than 50 nm,
   wherein the silver salt layer has a thickness of 50 nm to 500 nm.

2. The antimicrobial material of claim 1, wherein the porous activated ceramic substrate is activated alumina.

3. The antimicrobial material of claim 1, wherein the porous activated ceramic substrate has a surface area of more than 150 m$^2$·g-1.

4. The antimicrobial material of claim 1, wherein the titanium dioxide layer is less than 10% w/w of the antimicrobial material.

5. The antimicrobial material of claim 1, wherein the silver salt is a silver halide.

6. The antimicrobial material of claim 5, wherein the silver halide is a silver chloride.

7. The antimicrobial material of claim 1, wherein the silver salt layer is less than 10% w/w of the antimicrobial composition.

8. The antimicrobial material of claim 1, wherein the permanent electronic discharge of the silver salt layer is $10^{10}$ electrons per µm$^2$ of surface area of silver salt layer to $10^{12}$ electrons per µm$^2$ of surface area of silver salt layer.

9. An antimicrobial device comprising:
   a decontamination vessel manufactured from an antimicrobial material wherein the antimicrobial material is comprised of
   a porous activated ceramic substrate;
   a titanium dioxide layer covalently bound to the ceramic substrate wherein the titanium dioxide layer is a continuous layer covering the entire surface of the porous activated ceramic substrate; and
   a silver salt layer covalently bound to the titanium dioxide layer wherein the silver salt layer forms a discontinuous coating over the titanium dioxide layer, wherein the silver salt layer generates a permanent electronic discharge while remaining covalently bound to the titanium dioxide layer,
   wherein the titanium dioxide layer has a thickness of less than 50 nm,
   wherein the silver salt layer has a, thickness of 50 nm to 500 nm.

10. An antimicrobial device comprising:
    means for circulating a fluid to be decontaminated, wherein the means is comprised of fluid inlet means;
    a decontamination vessel in fluid communication with the fluid inlet means; and
    fluid outlet means in fluid communication with the decontamination means;
    an effective amount of an antimicrobial material confined in the decontaminating vessel wherein the antimicrobial material is comprised of
    a porous activated ceramic substrate;
    a titanium dioxide layer covalently bound to the ceramic substrate wherein the titanium dioxide layer is a continuous layer covering the entire surface of the porous activated ceramic substrate; and
    a silver salt layer covalently bound to the titanium dioxide layer wherein the silver salt layer forms a discontinuous coating over the titanium dioxide layer, wherein the silver salt layer generates a permanent electronic discharge while remaining covalently bound to the titanium dioxide layer,
    wherein the titanium dioxide layer has a thickness of less than 50 nm,
    wherein the silver salt layer has a, thickness of 50 nm to 500 nm.

11. A method for preparing an antimicrobial material comprising the steps of:
    a) providing a porous activated ceramic substrate;
    b) reacting the surface area of the porous activated ceramic substrate with titanium dioxide, wherein a titanium dioxide-coated solid ceramic substrate is obtained wherein the titanium dioxide layer is a continuous layer covering an entire surface of the porous activated ceramic substrate; and
    c) depositing a silver salt layer on the titanium dioxide-coated porous activated ceramic substrate obtained at step b wherein the silver salt layer forms a discontinuous coating over the titanium dioxide layer, wherein the silver salt layer generates a permanent electronic discharge while remaining covalently bound to the titanium dioxide layer;
    wherein the antimicrobial solid material is obtained after step c;
    wherein the titanium dioxide layer has a thickness of less than 50 nm,
    wherein the silver salt layer has a thickness of 50 nm to 500 nm.

12. A method for reducing or eliminating microorganisms from a fluid susceptible to contain microorganisms comprising:

contacting the fluid with an antimicrobial material wherein the antimicrobial material is comprised of a porous activated ceramic substrate;

a titanium dioxide layer covalently bound to the ceramic substrate wherein the titanium dioxide layer is a continuous layer covering the entire surface of the porous activated ceramic substrate; and a silver salt layer covalently bound to the titanium dioxide layer wherein the silver salt layer forms a discontinuous coating over the titanium dioxide layer, wherein the silver salt layer generates a permanent electronic discharge while remaining covalently bound to the titanium dioxide layer;

wherein the titanium dioxide layer has a thickness of less than 50 nm, wherein the silver salt layer has a, thickness of 50 nm to 500 nm, wherein the contact with the antimicrobial material reduces or eliminates the microorganisms in the fluid.

13. The method of claim 12, wherein the microorganisms are selected from the group consisting of Gram+ and Gram− bacteria, spore and non-spore forming bacteria, vegetative and non-vegetative fungi, yeast, protozoa, micro-algae, viruses and any combination thereof.

* * * * *